US012099045B2

(12) United States Patent
Rubenstein et al.

(10) Patent No.: US 12,099,045 B2
(45) Date of Patent: Sep. 24, 2024

(54) FOCUSING AGENTS AND CALIBRATION TRANSPORTABILITY

(71) Applicant: Government of the United States as Represented by the Secretary of the Air Force, Wright-Patterson AFB, OH (US)

(72) Inventors: H. Mitchell Rubenstein, Beavercreek, OH (US); Anthony Qualley, Washington Township, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 950 days.

(21) Appl. No.: 16/951,626

(22) Filed: Nov. 18, 2020

(65) Prior Publication Data
US 2021/0140933 A1    May 13, 2021

Related U.S. Application Data

(60) Continuation-in-part of application No. 16/415,118, filed on May 17, 2019, now Pat. No. 11,215,596, (Continued)

(51) Int. Cl.
*G01N 33/00* (2006.01)
*B01D 53/02* (2006.01)
(Continued)

(52) U.S. Cl.
CPC ....... *G01N 33/0057* (2013.01); *B01D 53/025* (2013.01); *G01N 1/405* (2013.01); (Continued)

(58) Field of Classification Search
CPC .... G01N 33/0057; G01N 1/405; G01N 30/08; G01N 30/7206; G01N 30/8668; G01N 33/0006; B01D 53/025
See application file for complete search history.

(56) References Cited

U.S. PATENT DOCUMENTS 8,383,420 B2    2/2013  Kingston et al.
2002/0055184 A1    5/2002  Naylor et al.
(Continued)

OTHER PUBLICATIONS

United States Patent and Trademark Office, Non-Final Office Action in U.S. Appl. No. 17/381,810, mailed Dec. 22, 2022, 7 pages total.
(Continued)

*Primary Examiner* — Brian R Gordon
*Assistant Examiner* — Dwan A Gerido
(74) *Attorney, Agent, or Firm* — AFMCLO/JAZ; James F. McBride

(57) ABSTRACT

A thermal desorption tube for chromatography and mass spectrometry analysis. The thermal desorption tube includes a sorbent and a plurality of focusing agents loaded at known, relative amounts onto the sorbent. Each focusing agent is a compound that chromatographically elutes within a retention time similar to a retention time of a target analyte and has a mass spectrum similar to a mass spectrum of the target analyte. The thermal desorption tube is configured to be further loaded with a sample having the target analyte.

4 Claims, 18 Drawing Sheets

Related U.S. Application Data which is a division of application No. 15/451,438, filed on Mar. 7, 2017, now Pat. No. 11,099,165.

(60) Provisional application No. 62/936,962, filed on Nov. 18, 2019, provisional application No. 62/305,395, filed on Mar. 8, 2016.

(51) Int. Cl.
    *G01N 1/40*       (2006.01)
    *G01N 30/08*      (2006.01)
    *G01N 30/72*      (2006.01)
    *G01N 30/86*      (2006.01)
    *G01N 30/02*      (2006.01)

(52) U.S. Cl.
CPC ......... *G01N 30/08* (2013.01); *G01N 30/7206* (2013.01); *G01N 30/8668* (2013.01); *G01N 33/0006* (2013.01); *G01N 2030/025* (2013.01); *G01N 2030/085* (2013.01)

(56) References Cited

U.S. PATENT DOCUMENTS

| | | | |
|---|---|---|---|
| 2006/0094118 A1 | 5/2006 | Tipler | |
| 2011/0111513 A1 | 5/2011 | Baumann et al. | |
| 2014/0238107 A1* | 8/2014 | Chou | G01N 33/0075 73/23.36 |
| 2015/0300928 A1 | 10/2015 | Perez Ballesta | |
| 2016/0203963 A1 | 7/2016 | Green | |

OTHER PUBLICATIONS

United States Patent and Trademark Office, Non-Final Office Action in U.S. Appl. No. 15/451,438, mailed Mar. 17, 2021, 12 pages total.
W. Hao et al., "Quantification of persistent organic pollutants in human whole blood samples using stir bar soprtive extraction coupled with GC/MS/MS and isotope dilution mass spectrometry," Microchemical J., vol. 153 (2020) 104279.
T. Fahrenholz et al., "Molecular speciated isotope dilution mass spectrometric methods for accurate, reproducible and direct quantification of reduced, oxidized and total glutathione in biological samples," Anal. Chem., 87 (2015) 1232-1240.
D. A. Cataldo et al., "Acute Environmental Toxicity and Persistence of Dem, A Chemical Agent Simulant: Diethyl Malonate," Final Report on Project Order No. 0311-1460, 1990.
W. A. Carrick et al., "Retrospective identification of chemical warfare agents by high-temperature automatic thermal desorption—gas chromatography-mass spectrometry," J. Chroma. A 925 (2001), pp. 241-249.
T. Hartman, "Methodologies For the Quantification of Purge and Trap Thermal Desorption and Direct Thermal Desorption Analyses," Application Note #9; http://www.sisweb.com/referenc/applnote/app-9.htm, 1999, 13 pp.
S. Harshman et al. "The stability of Tenax TA thermal desorption tubes in simulated field conditions on the HAPSITER® ER," International Journal of Environmental Analytical Chemistry 95(11): 1014-1029—Aug. 2015.
K. Demeestere et al., "Quality control in quantification of volatile organic compounds analysed bY thermal desorption-gas chromatography-mass spectrometry," J_Chroma_A 1186 (2008) pp. 348-357.
D. E. Tobias et al., "Direct thermal desorption of semivolatile organic compounds from diffusion denuders and gas chromatographic analysis for trace concentration measurement," J. Chroma. A 1140 (2007) pp. 1-12.
EPA 600/R-13/044, May 2013, "Stability Study for Ultra-Dilute Chemical Warfare Agent Standards," 45 pages.
K. Lundgren et al. "Low-resolution mass spectrometric relative response factors (RRFs) and relative retention times (RRTs) on two common gas chromatographic stationary phases for 87 polychlorinated dibenzofurans," Chemosphere 55, (2004), pp. 983-995.
N. G. Alonso, University of Oviedo, "Introduction to Isotope Dilution Analysis," Slides—40 pages, about 2010.
United States Patent and Trademark Office, Non-Final Office Action in U.S. Appl. No. 16/415,118, mailed Apr. 29, 2021, 9 pages total.
McLafferty "Interpretation of Mass Spectra" 2nd 1973, 108-109.

* cited by examiner

FOCUSING AGENTS AND CALIBRATION TRANSPORTABILITY

RELATED APPLICATION

The present application is a continuation-in-part application of co-pending U.S. application Ser. No. 16/415,118, filed May 17, 2019 (pending), which was a divisional of U.S. application Ser. No. 15/451,438, filed Mar. 7, 2017 (pending), which claims priority to U.S. Provisional Patent Application Ser. No. 62/305,395 filed Mar. 8, 2016. This application also claims benefit of and prior to U.S. Provisional Application Ser. No. 62/936,962, filed Nov. 18, 2019. The disclosure of each of these applications is hereby incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The invention is related to improved analytical techniques useful for the identification and enhanced quantification of chemical species, such as chemical warfare agents.

BACKGROUND OF THE INVENTION

The detection and quantification of chemical warfare agents ("CWAs") and toxic industrial chemicals/materials ("TIC/TIM") require field analysis reliance on previously established calibration curves programmed on field instruments. Sampling tubes constructed with adsorbent materials (which are better known as thermal desorption tubes ("TD")) are currently employed for field investigations, and the measured values of the CWAs, TICs, and TIMs demonstrate wide variability when control studies measure relative standard deviation ("RSD").

Accordingly, disconnects exist between analyses completed in the field and final analysis; therefore, resulting data has high variability and therefor lower reliability. For example, current studies employing an exemplary portable gas chromatograph-mass spectrometer ("GC/MS") HAPSITE ER (Inficon GMBH) demonstrate wide variability of data. This variability is observed both for intra- and inter-instrumental analyses. Current experiments have demonstrated RSD of about 70%, where the industry standard is generally about 30% RSD or less. This elevated uncertainty is especially surprising considering the device houses a canister of an internal standard (i.e., bromopentafluorobenzene) that is capable of being injected on each sample analysis. Similar variability has been observed with comparable devices from other manufacturers.

Accordingly, there is a need for new testing protocols and equipment to enhance the reliability of these field measurements.

SUMMARY OF THE INVENTION

The present invention overcomes the foregoing problems and other shortcomings, drawbacks, and challenges of analyzing data using a transportable device with its internal reference and calibration standard. While the invention will be described in connection with certain embodiments, it will be understood that the invention is not limited to these embodiments. To the contrary, this invention includes all alternatives, modifications, and equivalents as may be included within the spirit and scope of the present invention.

According to an embodiment of the present invention, a thermal desorption tube for chromatography and mass spectrometry analysis that includes a sorbent and a plurality of focusing agents loaded at known, relative amounts onto the sorbent. Each focusing agent is a compound that chromatographically elutes with a retention time similar to a retention time of a target analyte and has a mass spectrum similar to the mass spectrum of the target analyte. The thermal desorption tube is configured to be further loaded with a sample having the target analyte.

Yet another embodiment of the present invention is directed to a method of analyzing a sample for a target analyte using chromatography and mass spectroscopy. The method includes loading a sample having the target analyte onto a thermal desorption tube. The thermal desorption tube has a sorbent therein and a plurality of focusing agents loaded at known, relative amounts. Each focusing agent is a compound that chromatographically elutes with a retention time similar to a retention time of a target analyte and has a mass spectrum similar to the mass spectrum of the target analyte. The target and the plurality of focusing agents are desorbed from the sorbent and into the chromatography and mass spectrometry instrument. A response due to the target analyte is evaluated relative to the responses of the plurality of focusing agents.

Yet another embodiment of the present invention is directed to a method of comparing amounts of a target analyte using calibration transportability. First and second thermal desorption tubes are prepared with the same focusing agents at the same known, relative amounts. A first sample having the target analyte is acquired with the first thermal desorption tube; a second sample having the target analyte is acquired with the second thermal desorption tube. An amount of target analyte in each of the first and second samples is analyzed on different instruments and the amounts compared.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawing, which are incorporated in and constitute a part of this specification, illustrate embodiments of the invention and, together with a general description of the invention given above, and the detailed description given below, serve to explain the invention. It will be appreciated that for purposes of clarity and where deemed appropriate, reference numerals have been repeated in the figures to indicate corresponding features.

FIG. 7 exemplifies a stability of the focusing agents with respect to various curing temperatures in thermal desorption tube preparation.

Figure 1:
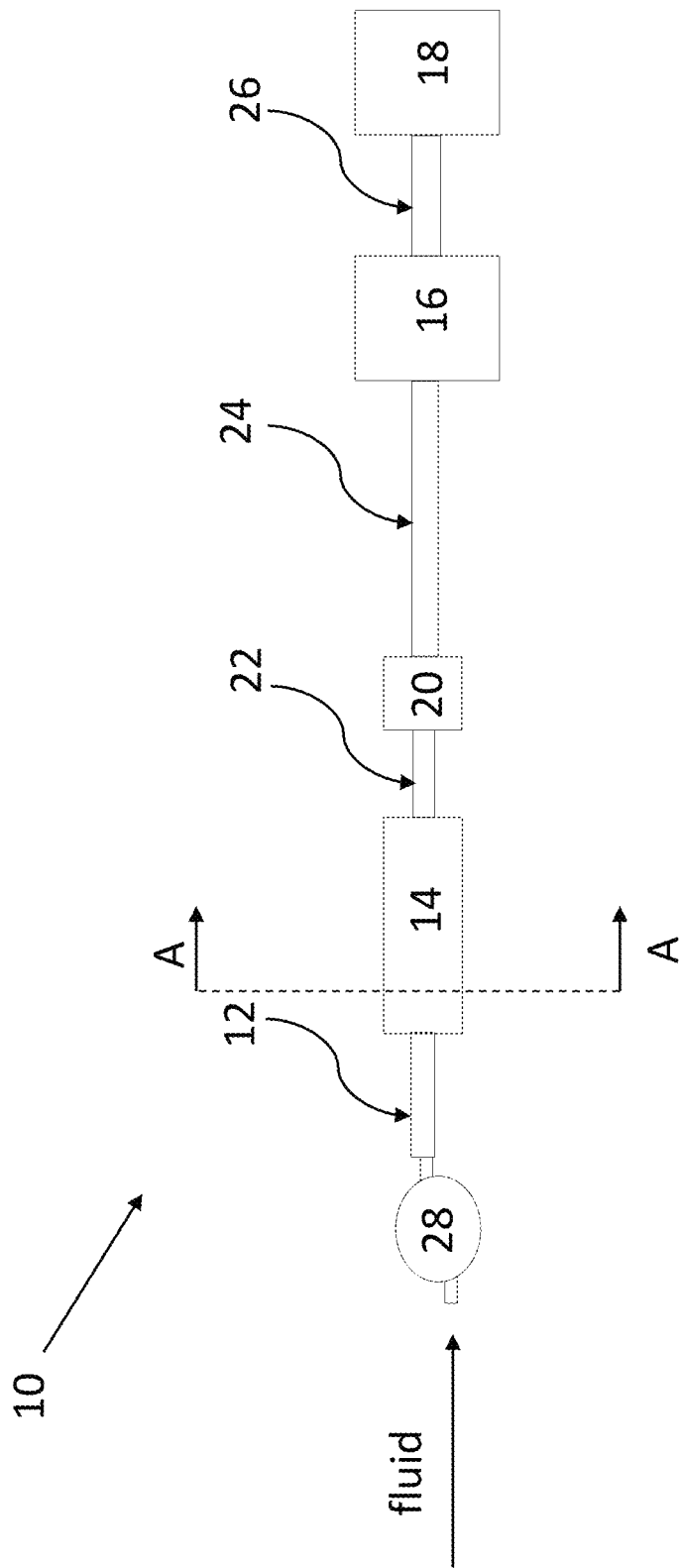
FIG. 1 is a schematic of a system for identifying and quantifying a chemical agent, in accordance with an embodiment of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

As used herein, "HAPSITE ER" is a person-portable gas chromatograph/mass spectrometer ("GC/MS") that has the capability to identify and quantify volatile organic compounds ("VOCs"), CWAs (chemical warfare agents), and select semi-volatile organic compounds ("SVOCs"). Generally speaking, use of portable GC/MS, such as HAPSITE ER, is limited to analytes having a boiling point ("BP") that is less than about 280° C.

As used herein, "thermal desorption" is a technique that concentrates organic compounds onto select media prior to injection in a GC (gas chromatograph).

As used herein, "adsorption" is a technique that concentrates VOCs and SVOCs onto select media, while "thermal desorption" describes the liberation of VOCs and SVOCs from the select media.

As used herein, "internal standard" is a chemical compound purposely added to samples and/or standards at a known concentration to provide a basis for comparison in quantitation.

As used herein, "simulant" includes compounds that simulate the chemistry and reactivity of CWAs but that have considerably lower relative toxicity.

As used herein, "analyte" includes chemical compounds of interest.

As used herein, "isotope dilution" means a method that improves quantitation of known compounds by the addition of known concentration of isotopically enriched substance(s) to the analyzed sample.

As used herein, "focusing agent" refers to compound(s) refers to compounds added to a thermal desorption ("TD") tube or other media, in accordance with embodiments of the present invention, to aid in correlating data acquired in the absence of instrument calibration. Focusing agents should chromatographically elute within the same retention time of the target analyte in either gas chromatography or liquid chromatography.

As used herein, "volatiles" or VOCs refers to organic compounds that have a vapor pressure of 0.01 kPa or more at 20° C.

As used herein, "semi-volatiles" or SVOCs refers to organic compounds that have a vapor pressure less than 0.01 kPa.

As used herein, "predetermined relative retention time ratio" or "predetermined RRT ratio" refers to a ratio of the retention times for the analyte ($RT_A$) with respect to the retention times for the focusing agent ($RT_{FA}$) using the analytical chromatographical testing procedure. More specifically, $RRT = RT_A/RT_{FA}$.

As used herein, "relative response factor" or "RRF" refers to a ratio of a signal produced by the analyte on a detector associated with the analytical chromatographic testing procedure and the quantity of analyte which produces that signal to a signal produced by the focusing agent and the quantity of the focusing agent which produces that signal. More specifically, RRF is a ratio of a (Response factor of analyte)/(Response factor of focusing agent).

As used herein, "LOD/LOQ" refers to "limit of detection" (LOD) and "limit of quantification" (LOQ), respectively. The LOD is generally defined as three times the standard deviation ("SD") of the blank; the LOQ is defined as ten times the SD of the blank. For a signal at the LOD, the alpha error (probability of false positive) is small (1%). However, the beta error (probability of a false negative) is 50% for a sample that has a concentration at the LOD (3×SD). This means a sample could contain an impurity at the LOD, but there is a 50% chance that a measurement would give a result less than the LOD. At the LOQ (10×SD), there is minimal chance of a false negative.

With reference now to FIG. 1, a schematic of a system 10 for identifying and quantifying a chemical agent is shown. The system 10 includes a conduit 12 fluidly coupled to an analytical sampling device 14 operably connected to chromatographic subsystem 16 and a mass spectrometer subsystem 18. Optionally, a pre-concentrator 20 may be positioned between the analytical sampling device 14 and the chromatographic and mass spectrometer subsystems 16, 18. A pump 28 may be used to transfer a fluid sample comprising the chemical agent into contact with the analytical sampling device 14. Conduits 12, 22, 24, 26 provide fluid connections between the components of the system 10.

Figure 2:
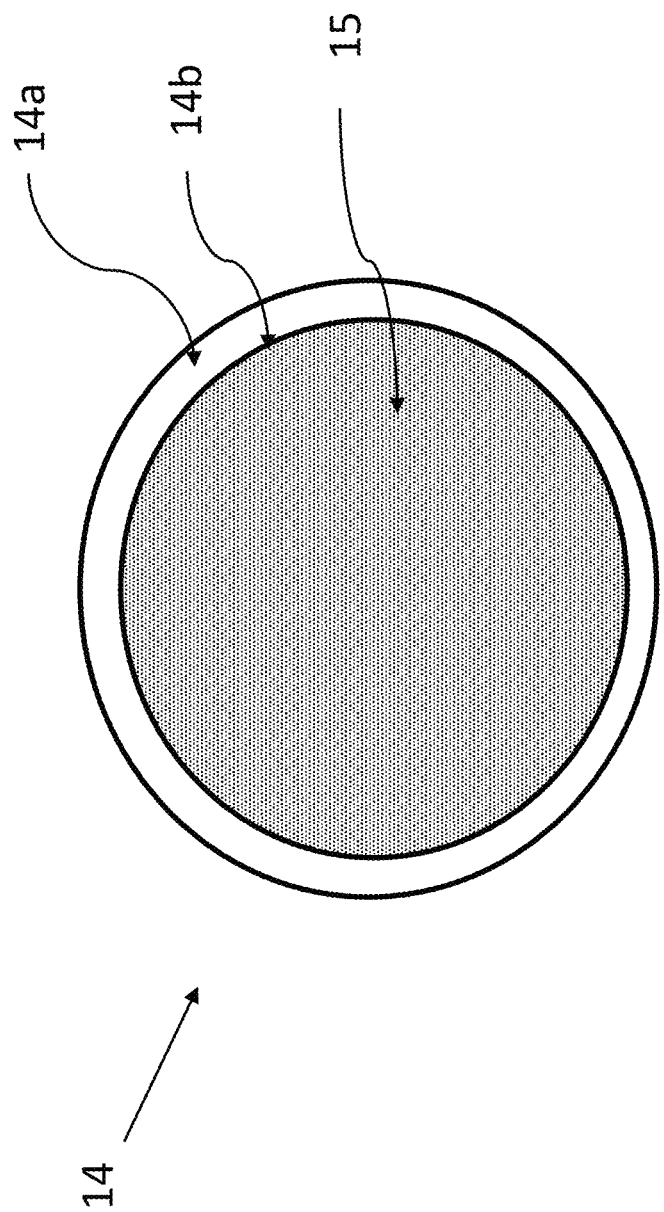
FIG. 2 is cross-sectional view of an analytical sampling device of the system shown in FIG. 1, taken along line A-A.

With reference to FIG. 2, a cross-sectional view of the analytical sampling device 14 is shown, where an outer structure 14a having an inner surface 14b contains an adsorbent media or material, into which is adsorbed the focusing agent to form an embedded focusing agent region 15.

The embedding of focusing agents into the TD tubes (or other media) advances the technology of analytical field measurements. To date multiple media has been employed to capture a variety of analytes. In accordance with embodiments described herein, we further examined stability of the exemplary embedded focusing agents, as well at the variability of the analytical chromatographical testing method, utilizing the HAPSITE ER (INFICON GMBH). However, the embodiments and the inventive principles described herein relate to thermal desorption techniques from all manufacturers. Furthermore, the incorporation of focusing agents may be applicable to all adsorbent media types and to other analytical techniques.

Embodiments of this invention incorporate compounds of known or established concentration onto the adsorbent media of the analytical sampling device, such as TD tubes comprising a sorbent. While the present studies concentrated on thermal desorption using TENAX-TA resin, this technique can be extended to a wide variety of media currently employed by industry. Typical types of adsorbent materials include, but are not limited to, alumina, silica, carbon-containing adsorbents, a zeolite, a porous glass, a clay, a porous polymer based on 2,6-diphenyl-p-phenylene oxide, a hydrophobic copolymer of styrene-divinylbenzene resin, a polyurethane, or a combination thereof. More specifically, adsorbent materials of principal interest include alumina, FLORISIL or other silicas, any of cyanopropyl, diol, porous glassy carbon, or HYPERSIL-ODS, all available from Keystone Scientific, Bellefonte, Pa., TENAX-TA available from Enka Research Institute of Holland, polyurethane foam, diatomaceous earth and zeolites. As will be appreciated by those of skill in the art, the choice of the adsorbent material depends on the nature of the focusing agent and the analyte(s), as well as the ability of the analytical chromatographical testing procedure to liberate the adsorbed focusing agents and analyte(s) from the adsorbent media.

For example, silica gel tubes, ANASORB sorbent tubes, charcoal sorbent tubes, TENAX sorbent tubes, XAD sorbent tubes, CHROMOSORB sorbent tubes, polyurethane foam ("PUF") tubes, PORAPAK sorbent tubes, OSHA Versatile Sampler ("OVS") sorbent tubes, or other sorbent tubes including alumina, carbon beads, drying tubes, firebrick, FLORISIL, glass beads, molecular sieve and soda lime tubes are known or commercially-available.

In one example, the TD tubes comprise TENAX TA, which has been stabilized for both sample volume collected and elevated temperatures that would be anticipated in U.S. military global surveillance. The adsorbent media can then be used to normalize data from sample to sample collected and analyzed. The experiments performed in accordance with embodiments of the present invention, show significant improvement in the quality of the data as measured by RSD.

A process for incorporating focusing agents onto the adsorbent media of the analytical sampling device may include injecting the focusing agent in solution (such as with an organic solvent, such as acetonitrile) into the TD tubes. Such injection may include a commercially available Calibration Solution Loading Rig ("CSLR") from Markes International, Inc., Cincinnati, Ohio at 20 psi at approximately 60 mL/min; however other methods could be used. In accordance with an embodiment of the present invention, a focusing agent may be embedded into the analytical sampling device at temperatures ranging from about 35° C. to about 95° C. For example, the embedding temperature may be about 35° C., about 40° C., about 45° C., about 50° C., about 55° C., about 60° C., about 65° C., about 70° C., about 75° C., about 80° C., about 85° C., about 90° C., about 95° C., or in a range between any two of the foregoing. Once the TD tubes are loaded, the tubes may be dry conditioned at 50° C., 50 mL to 60 mL $N_2$ flow at 20 psi for 1.5 hours—which may include a Markes TC-20 (from Markes International, Inc., Cincinnati). The prepared, TD tubes may then be stored at room temperature.

Focusing agents are chosen based on their chromatographic similarity or spectral similarity to the chemical agent(s) (i.e., the analyst(s)) under investigation. As used herein, "chromatographic similarity" is based on the selected analytical method for testing. For an example involving GC/MS, chromatographic similarity is determined using a gas chromatography instrument. For an example involving LC/MS chromatographic similarity is determined using a liquid chromatography instrument. It is preferable that the Resolution ($R_s$) is sufficient to minimize interference between the signals of the focusing agents and any analytes:

$$R_s = 2(t_{RB} - t_{RA})/(w_B + w_A),$$

where: $t_{RB}$ is a retention time of solute B; $t_{RA}$ is a retention time of solute A; $w_B$ is a Gaussian curve width of solute B; and $w_A$ is a Gaussian curve width of solute A. Chromatographically, the only critical factor is that the compounds (i.e., the focusing agent(s) and the analyte(s)) elute under the same chromatographic analysis conditions. Therefore, for gas chromatographic subsystems 16 (FIG. 1), lower boiling compounds will require lower boiling focusing agents and higher boiling compounds will require mid to high boiling focusing agents. In accordance with an embodiment of the present invention, sufficient resolution of two chromatographically similar compounds is achieved by no overlap greater than at full width half max.

"Spectral similarity" is also based on the selected analytical method. Mass spectrometry is an analytical technique that ionizes chemical species and sorts the ions based on a mass-to-charge ratio. Hence, similar fragmentation may be achieved from related compounds. An example, benzene, toluene, and ethyl benzene fragment similarly and only differ by the increase in mass from the $CH_2$ groups (i.e., benzene with a MW of 78, toluene with a MW of 92, and ethyl benzene with a MW of 106). Accordingly, this attribute can be used for quantification using response factors ($R_f$), in that the compounds by mass spectral determination will provide similar $R_f$'s. Thus, in accordance with an embodiment of the present invention, a mass spectrometry subsystem 18 (FIG. 1) is utilized for analysis, and "spectral similarity" refers to a range of compounds in parent molecule of M+10 and its associated fragments, as reflected in its associate fragments. Focusing agents make use of this phenomenon and the appropriate choice should be based on compounds that behave similarly with regard to the fragmentation. It should be appreciated by those having ordinary skill in the art and the benefit of the disclosure made herein that the spectral similarity does not require structural similarity. Instead, the focusing agent will have a retention time and mass spectrum similar to the target analyte.

Finally, the method can be enhanced by using isotopic analogs of the target compounds or the focusing agent. Since mass spectral data can separate isotopic analogues, no previous calibration is required and each collected tube has a calibration embedded for analysis.

Table 1 provides exemplary focusing agents, simulants, and surrogates for various chemical agents using a GC/MS technique.

TABLE 1

| M/Z | RT | Focusing agent | Chemical Agent |
|---|---|---|---|
| 117 | 3.37 | Bromopentafluorobenzene (internal standard) | — |
| 75 | 4.45 | 2-Chloroethyl Ethyl Sulfide | Bis(2-chloroethyl)sulfide (HD) |
| 127 | 5.15 | Diisopropyl Fluoro Phosphate | Sarin (GB) |
| 79/97/125 | 5.59 | Diethyl Methyl Phosphonate | Sarin (GB) |
| 115 | 6.33 | Diethyl Malonate | General |
| 120 | 7.35 | Methyl Salicylate | General |
| 226/191 | 8.16 | Dichlorvos-d6 | General |
| 220/205 | 12.59 | Atrazine-d5 | Pyrethroids |

All chemicals were chromatographically identified using HAPSITE ER on the CWA profile as supplied. Atrazine-d5 was used as an internal standard for the analysis of transflutherin. The pyrethroid analyses were conducted on a Thermo-Fisher TSQ mass GCMS. The method used was the commercially-available method by Inficon for CWA analysis.

Figure 3:
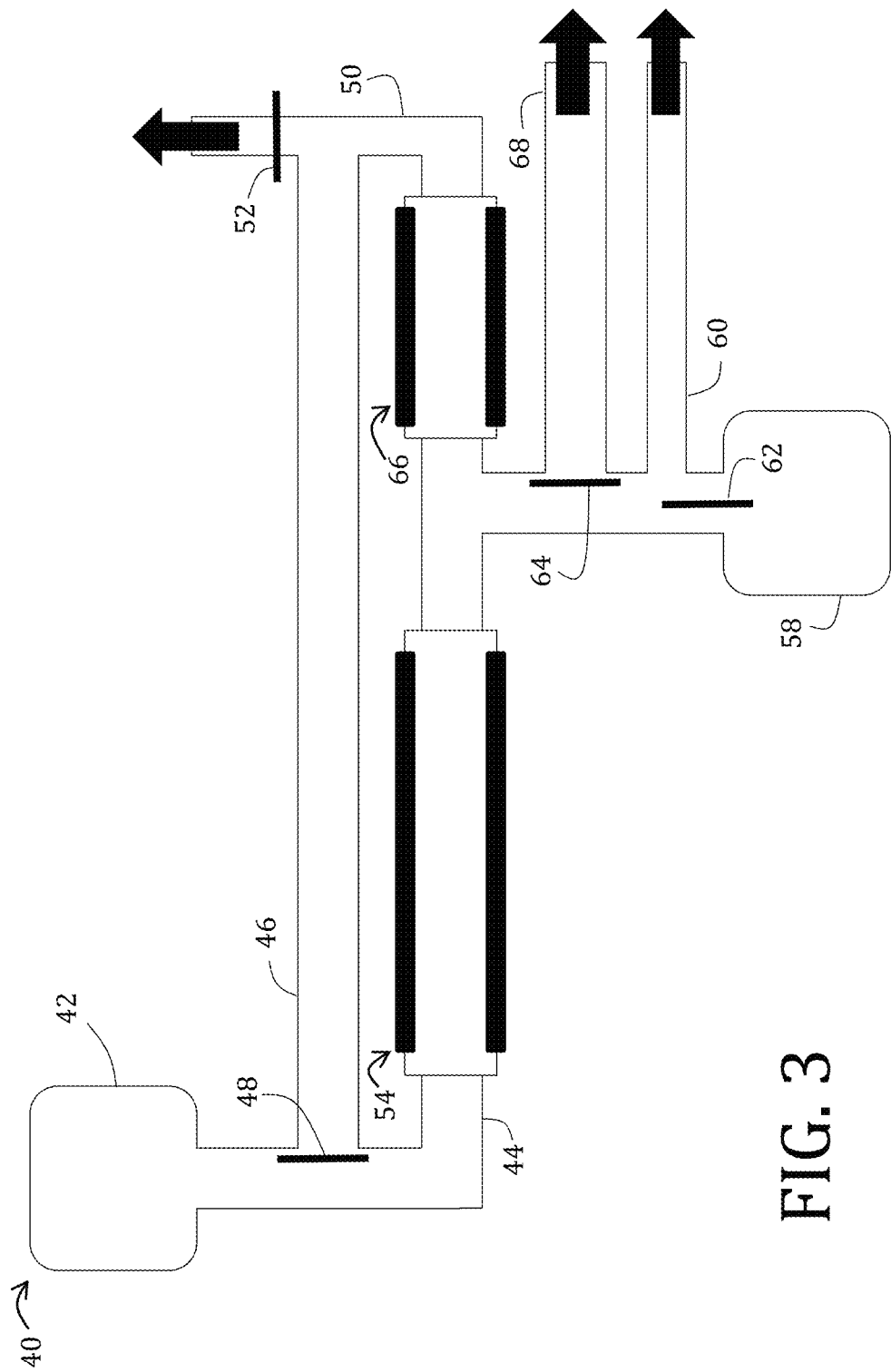
FIG. 3 is a schematic view of a system for identifying and quantifying a chemical agent, in accordance with an embodiment of the present invention.

Referring now to FIG. 3, a schematic representation of flow paths for a conventional portable gas chromatography-mass spectrometer 40. A carrier gas supply 42 may be operably coupled to a first flow line 44 and a second flow line 46 with a first valve 48 between the first and second flow lines 44, 46 (illustrated as the first valve 48 closing off the second flow line 46). The instrument may be flushed by flowing carrier gas through the first and second flow lines 44, 46 to a first vent line 50 having a second valve 52. When sampling is desired, carrier gas flows into the first flow line 44 and into a TD sampling system ("TDSS") 54.

An internal standard may be released from an internal standard supply 58. Conventionally, a first portion of the internal standard flows into the first flow line 44 while a second portion of the internal standard flows to a second vent line 60 (when third and fourth valves 62, 64 are open). The focusing agents, the sample, and the internal standard collect within a concentrator 66 along the first flow line 44.

For analysis, carrier gas flows through the second flow line 46 (the first valve 48 is used to close off the first flow line 44), through the first vent line 50 and to the first flow line 44 and the concentrator 66. The focusing agents, sample, internal standard, and carrier gas then flow from the concentrator 66 to an instrument line 68 (third and fourth valves 62, 64 close off the second vent line 60 and the internal standard supply 58 while opening the instrument line 68).

Figure 4A:
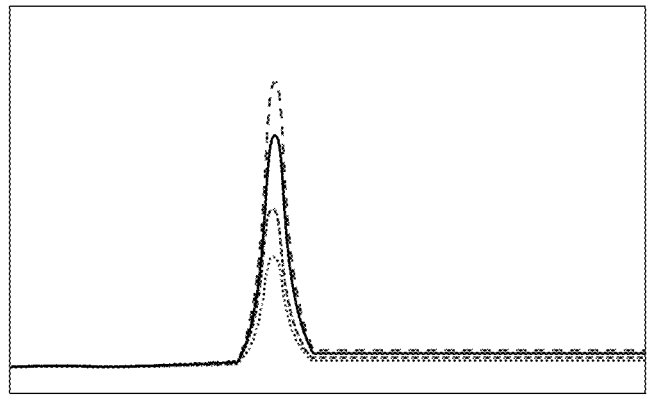
FIGS. 4A and 4B are graphical representations of exemplary data acquired in accordance with an embodiment of the present invention from two separate instruments.
Figure 4B:
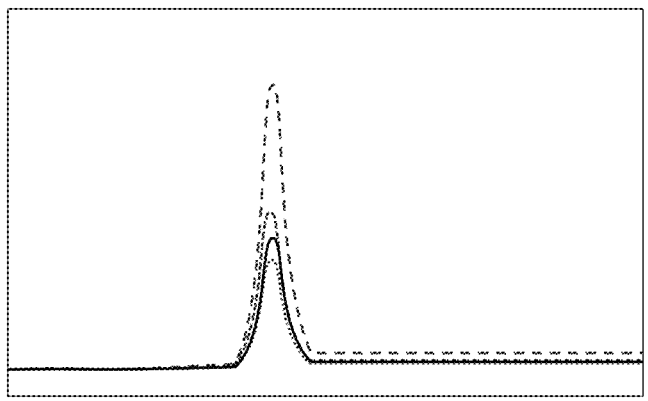
Figure 4C:
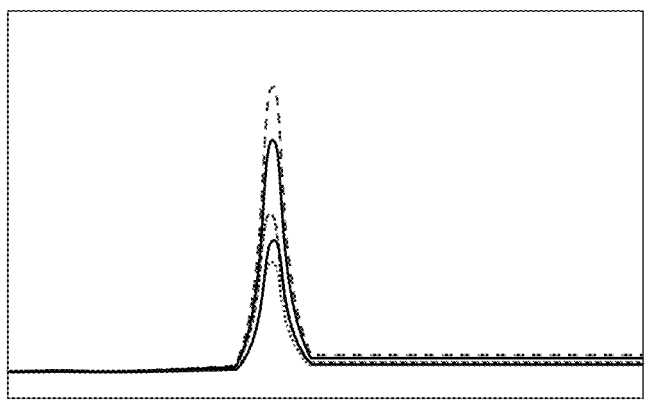
FIG. 4C is a graphical representation of the exemplary data from FIGS. 5A and 5B, overlain to demonstrate transportability of the focusing agent calibration.

FIGS. 4A-4C are graphical representations of exemplary data resulting from analysis by a first instrument with a first TD tube (FIG. 4A) and a second instrument with a second TD tube (FIG. 4B). In these figures, the grey, dotted, short dashed, and long dashed lines represent signal from the focusing agents at known concentrations. The solid, black line in FIG. 4A represents the signal resulting from a first sample collected and analyzed on the first instrument; the solid, black line in FIG. 4B represents the signal resulting from a second sample collected and analyzed on the second instrument.

Figure 5:
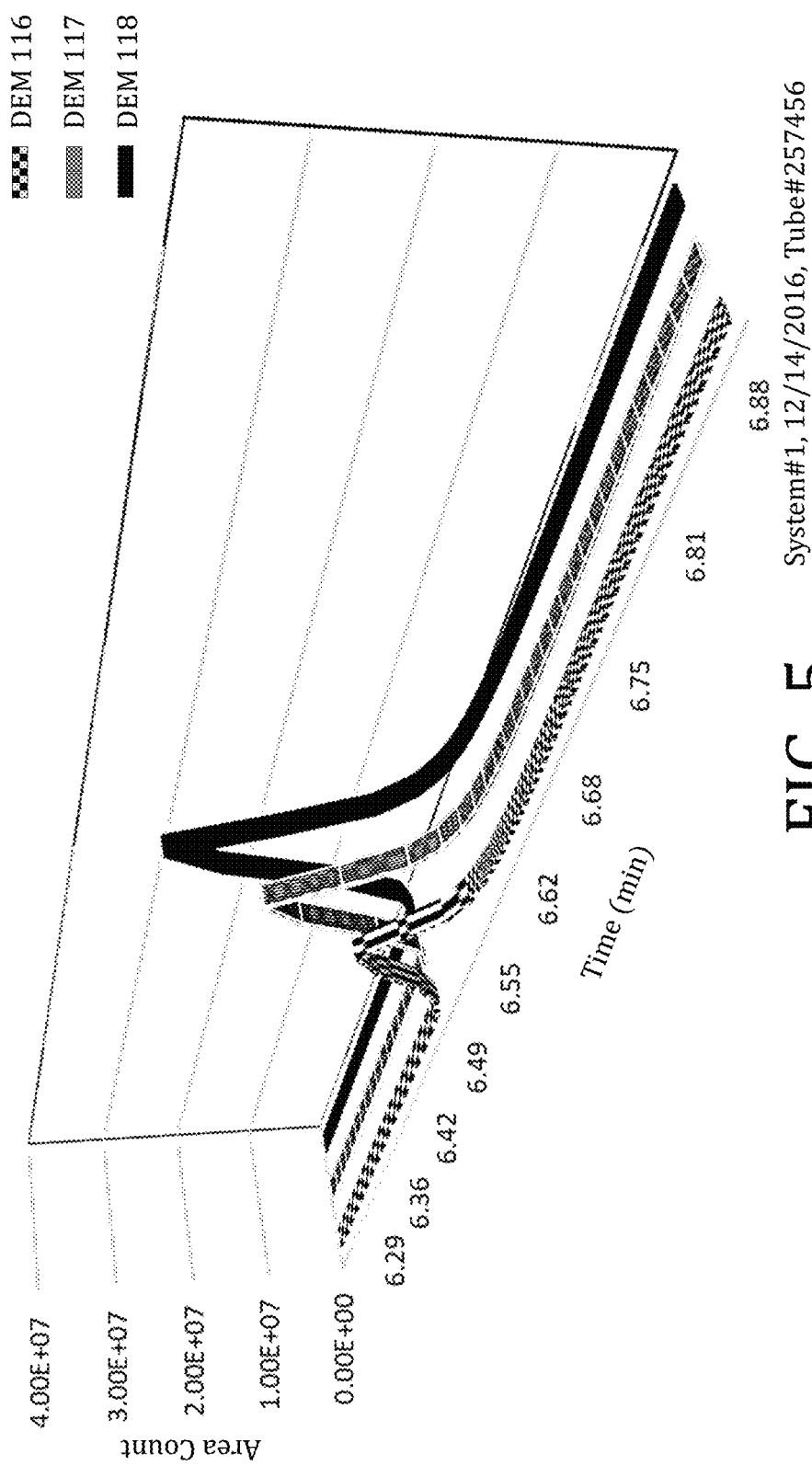
FIG. 5 is a three-dimensional plot of data showing a three-point curve of an analytical sampling device embedded with a focusing agent comprising three C-13 isotope analogs of diethyl malonate, where the data was obtained with a system and method in accordance with embodiments of the present invention.

Those of ordinary skill in the art having the benefit of the disclosure made herein will readily appreciate that because the relative amounts of focusing agents are the same for the first and second TD tubes, and $r^2$ values of an associated calibration curve approach 1, the values obtained for the first and second samples may be compared despite being analyzed by two separate instruments (see FIG. 5C). Conventionally, when only the internal standard (that is, an internal standard that is incorporated into the instrument) is utilized, such comparison is impracticable-to-impossible due to variability in an amount of internal standard that is loaded into the concentrator. This variability exists between instruments and may exist between data runs on the same instrument. Other internal standards, i.e., those added to a sample prior to analysis, require multiple injections that may introduce user error, are often used merely for setting an m/z value, and cannot allow for comparison of results across instruments.

It should further be appreciated by the skilled artisan having the benefit of the disclosure made herein that as the $r^2$ values approach 1, a single focusing agent value may be used to represent the calibration curve.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

Sarin is an organophosphorus compound with the formula $(CH_3)_2CHOCH_3P(O)F$. Sarin (or "GB") is a colorless, odorless liquid, used as a chemical weapon owing to its extreme potency as a nerve agent. It can be lethal even at very low concentrations, where death can occur within one-to-ten minutes after direct inhalation of a lethal dose due to suffocation from lung muscle paralysis. Antidotes, typically atropine and an oxime, such as pralidoxime, should be quickly administered. Sarin is generally considered a weapon of mass destruction. Production and stockpiling of sarin was outlawed as of April 1997 by the Chemical Weapons Convention of 1993, and it is classified as a Schedule 1 substance. In June 1994, the United Nations Special Commission on Iraqi disarmament destroyed the nerve agent sarin under Security Council resolution 687 (1991) concerning the disposal of Iraq's weapons of mass destruction. Accordingly, sarin is an exemplary chemical agent that may be detected and quantified in accordance with embodiments of the present invention.

Diisopropyl fluoro phosphate ("DIFP", a non-schedule 1 compound) bears a close relationship to sarin ("GB"), varying structurally by the replacement of the methyl group in sarin with an isopropoxy group. Due to this similarity, DIFP may be used as a focusing agent for GB. At start, a calibration curve of sarin and DIFP would be created on a first instrument. Field measurements may then be acquired using a second instrument having an analytical sampling device having a known concentration of DIFP, which would be used when testing a sample having an unknown concentration or quantity of sarin. The concentration can then be determined by correlation. Another similar correlation can be drawn between mustard gas ("HD") and 2-chloroethyl ethyl sulfide ("CEES").

All chemicals were chromatographically identified using the HAPSITE ER on the CWA profile as supplied. Atrazine-d5 was used as an internal standard for the analysis of transflutherin (unpublished). The pyrethroid analyses were conducted on a Thermo-Fisher TSQ mass GC/MS. The method used was the commercially available method provided by Inficon for CWA analysis.

Example 2

Diethyl malonate (MW 160) was selected as a model chemical agent with focusing agents including diethyl malonate-2-$^{13}$C, diethyl malonate-1,2-$^{13}$C, or diethyl malonate-1,2,3-$^{13}$C, having MW 161, 162 and 163, respectively. The m/z ions (base peak) of the focusing agents for quantification can be 116, 117 and 118, respectively, and are referred hereafter as $DEM_{116}$, $DEM_{117}$, and $DEM_{118}$, respectively. The base peak would be understood to be the most intense (tallest) peak in a mass spectrum due to the ion with the greatest relative abundance. Base peaks are not always molecular ions and molecular ions are not always base peaks.

Figure 6:
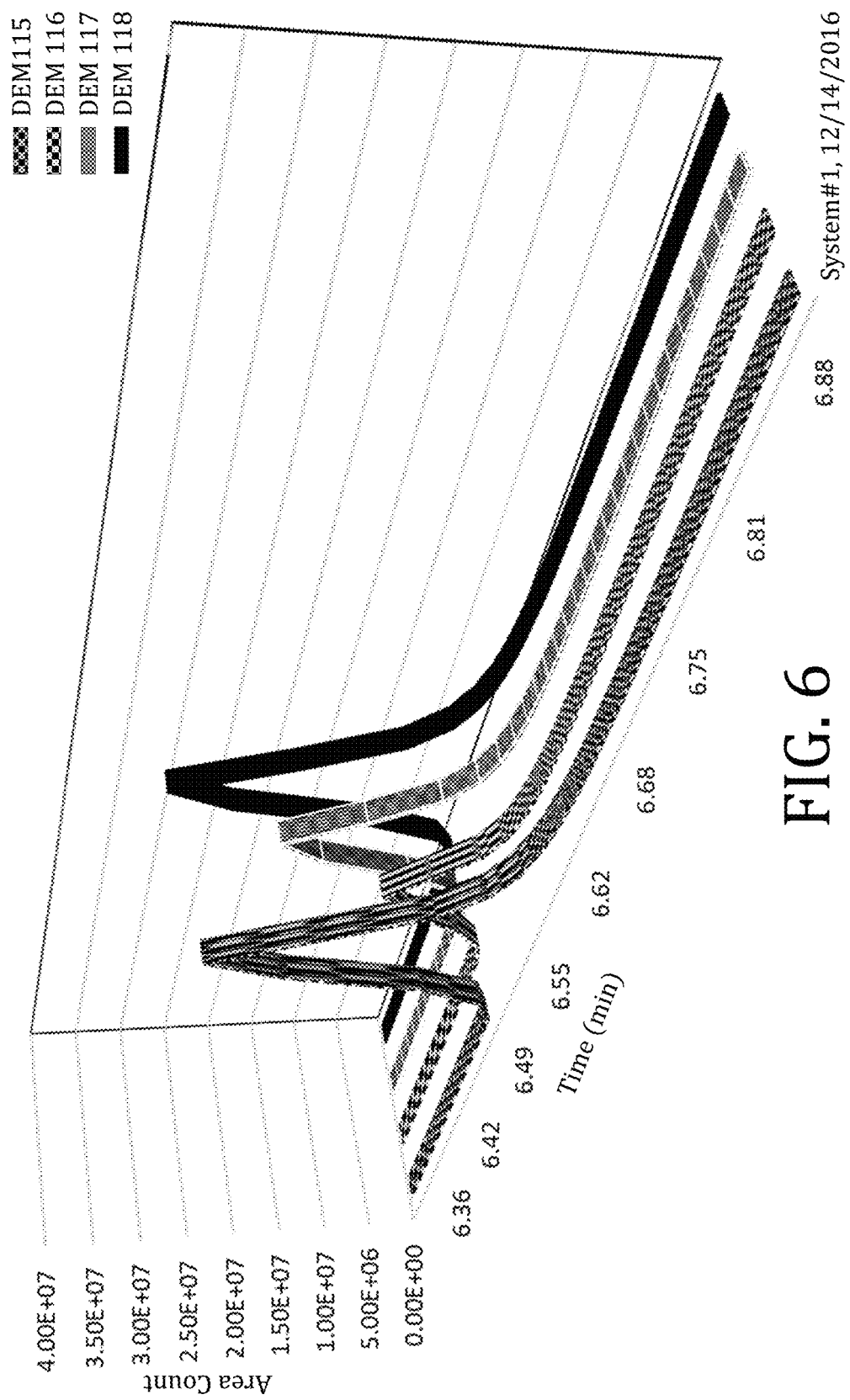
FIG. 6 is a three-dimensional plot of data of a three-point curve of an analytical sampling device applied with test sample of diethyl malonate, where the analytical sampling devices was previously embedded with a focusing agent comprising three C-13 isotope analogs of diethyl malonate, where the data was obtained with a system and method in accordance with embodiments of the present invention.

The tubes were loaded, as described above, with $DEM_{116}$, $DEM_{117}$, and $DEM_{118}$ at 1:2:3 ratio concentrations, respectively, and stored at room temperature. Analyses were conducted over a period of one month at a minimum of three points. FIG. 6 illustrates a three-point calibration curve using 1:2:3 ratio concentrations of $DEM_{116}$, $DEM_{117}$, and $DEM_{118}$, as shown in FIG. 6.

Figure 7:
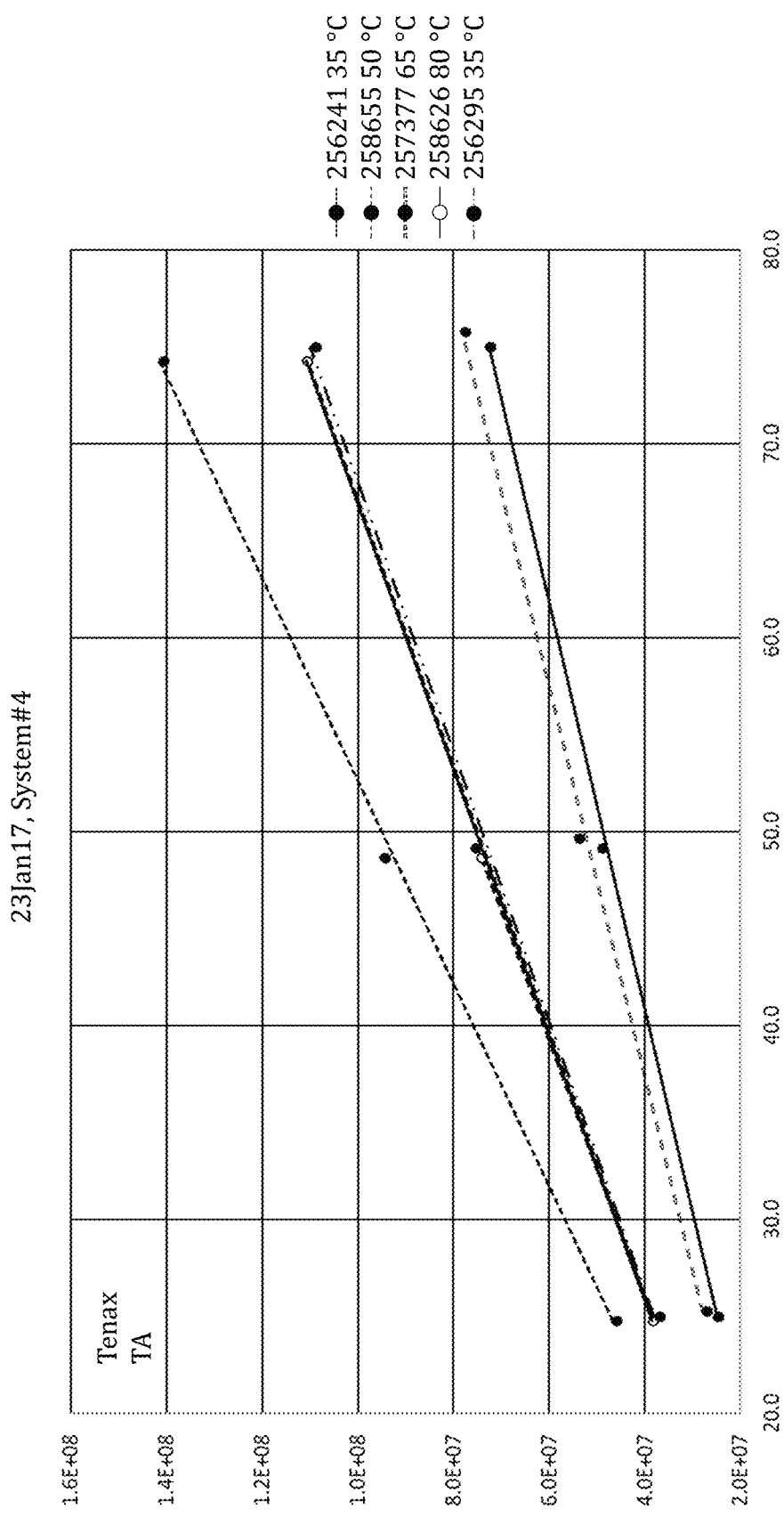
FIG. 7 is a linear plot of the focusing agent comprising three C-13 isotope analogs of diethyl malonate, where analysis was performed on three instruments over three months in triplicate to demonstrate the linearity, reproducibility, and stability of the system of the embodiments of the present invention.
Figure 10:
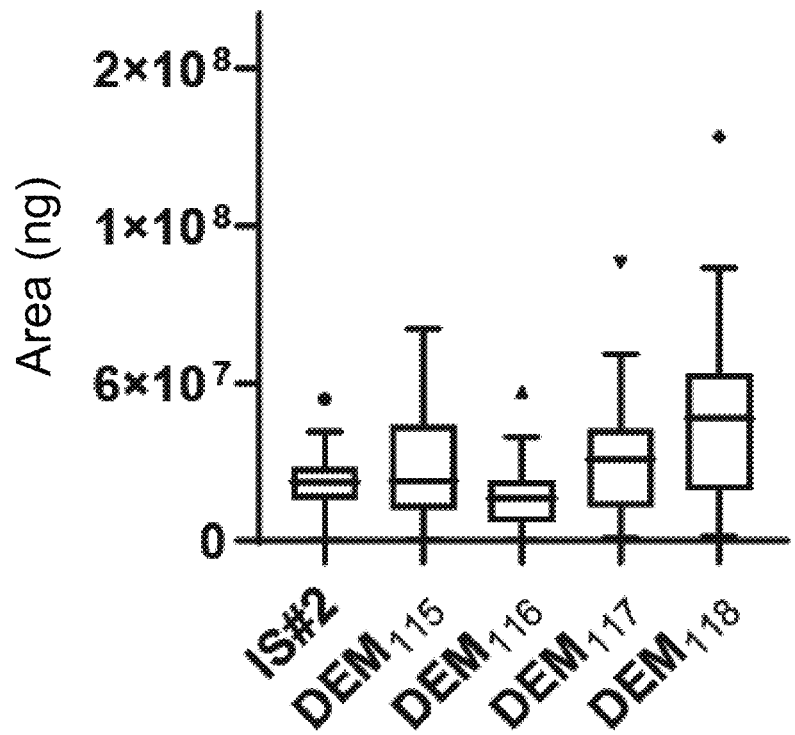
FIGS. 10 and 11 graphically illustrate a distribution of peak area responses for each analyte, which illustrate the frequent disparities observed in the IS #2 response, with FIG. 10 illustrating raw data and FIG. 11 illustrating normalized data.

These in-situ embedded tubes can then be used to collect the native diethyl malonate (MW 160) with an m/z ion at 115 (hereafter, $DEM_{115}$). As shown in FIG. 7, $DEM_{115}$ signal overlays signals from $DEM_{116}$, $DEM_{117}$, and $DEM_{118}$. Using the relative signals of $DEM_{116}$, $DEM_{117}$, and $DEM_{118}$, and the known concentration of these focusing agents in the tube, a three-point curve may be determined with $r^2$ values of 1.0000±0.0015 yielding RSDs of less than or equal to 5%. In this manner field equipment can achieve results equal to or surpassing fix-based laboratory data. This technique can also be used as a diagnostic tool for the on-going examination of laboratory equipment. Quantitation has yielded remarkable recoveries at 100±5% (see FIG. 10).

The current work was based on the field detection and quantitation of CWAs, thus, the focusing agents were simulants that have previously been used in CWA work. It is our belief that the simulants which are semi-volatiles will have universality for other semi-volatiles that exhibit similar chromatographic similarities. Other focusing agents will be chosen dependent on the chemistry and chromatography of the chemicals of concern.

Example 3

Studies were performed to investigate the effect of loading temperature on the embedding process and stability of focusing agents on the analytical sampling device (e.g., a TD tube). The embedding experiments were conducted at about 35° C., about 50° C., about 65° C., about 80° C., and about 95° C. Excellent recoveries were observed at all temperatures but suppression was observed at an embedding temperature of about 35° C. This suppression may indicate that the acetonitrile used as solvent may not be completely removed.

Initial trials were done at a constant concentration of the focusing agent. Subsequent experiments were conducted by preparing the analytical sampling device under similar conditions, but at four concentration levels, where the fourth concentration may be a variable mount of the native DEM (m/z=115) that is introduced prior to analysis to determine a stability of the stored tubes. Stability was measured over a period of one month. The conditions chosen represented the highest field temperature conditions expected. The concentrations were chosen based on the response of the focusing agent over a minimum of three instruments.

When the procedure for adsorbing the exemplary focusing agents onto a TENAX TA resin is followed, the focusing agent has been shown to be stable for over 1 month or more (e.g., two months, three months or more) at room temperature. Further stability testing approximated harsh sampling conditions and, again, the focusing agent on the media was stable at 60 mL/min at 50° C. for 1.5 hours. The process has demonstrated the viability of the addition of a focusing agent, sampling under elevated temperatures. Under analytical conditions for thermal desorption, the focusing agents were released and virtually quantitative recoveries were observed. Tubes prepared in this manner are expected to be used under a variety of field conditions and/or for samples returned to the laboratory. Since it adds a known substance at a prescribed concentration, it will also assist with determining quantities for unknown compounds that were not calibrated.

Figure 8:
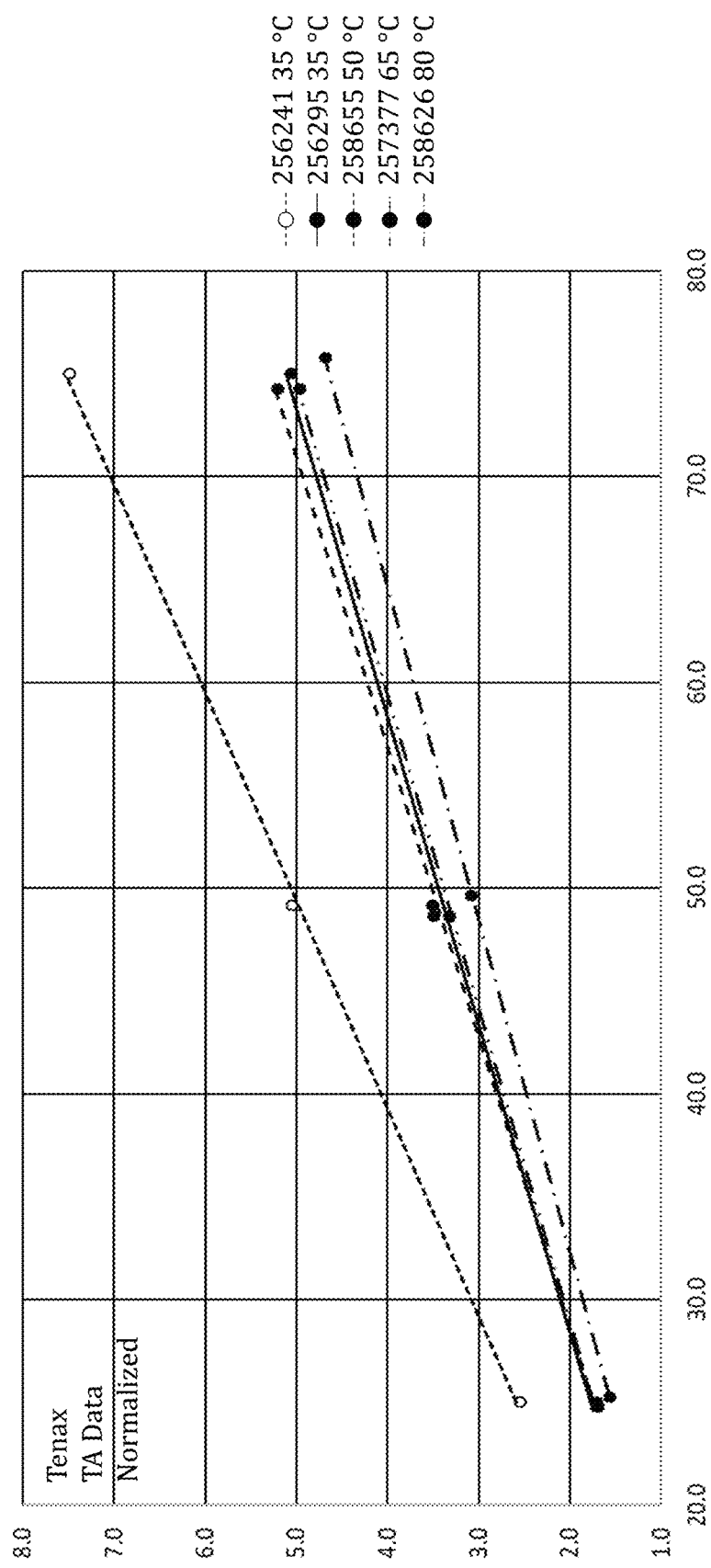
FIG. 8 is a linear plot showing normalization of data from in FIG. 8.
Figure 9:
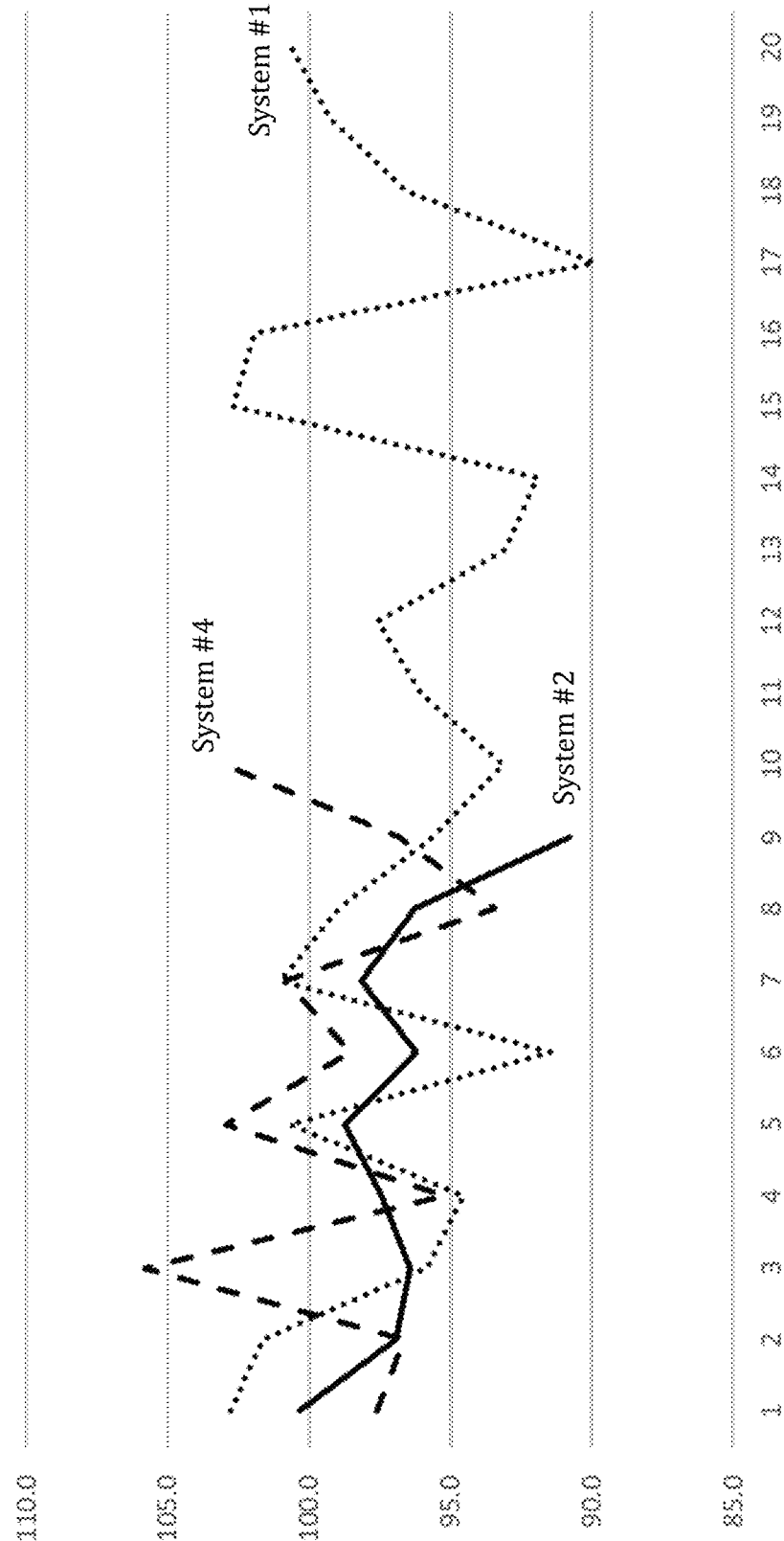
FIG. 9 is line plot showing percent recoveries of the embedded focusing agents comprising three C-13 isotope analogs of diethyl malonate, which demonstrates a stability of the focusing agents over time.

Results are shown in FIGS. 7 and 8. Current experiments have demonstrated reduction of variability as measured by RSD from 70% to less than 20%, where the industry standard is generally less than 30% RSD.

The Focusing Agents that track sampling from field collection to laboratory/field analysis could be applied to a variety of media packed in a multitude of configurations (tubes, dosimeters, impingers, etc.). The technique could be used across a variety of analytical applications and is not just limited to gas chromatography mass spectrometry. It is immediately applicable to liquid chromatography ("LC") mass spectrometry and other LC techniques with some modification. Other analytical techniques may also benefit, but additional work on selection of focusing agents would be required.

Example 4

Internal Standard #2 (IS #2) and four isotopic analogues of DEM (diethyl malonate) were measured in this experiment. All variants of DEM were purchased from Sigma-Aldrich and had an isotopic purity of 99%. Stainless steel tubes (3.5 inches×0.25 inch) were, packed with TENAX-TA 35/60 mesh, were purchased from Markes International (Sacramento, CA, USA). HAPSITE-ER ("HER") systems 40 with the TDSS 54, concentrator 66, compressed canisters of nitrogen and internal standard mixture were obtained from Inficon (East Syracuse, NY, USA). All TD tubes were conditioned before use as described by the manufacturer.

Prior to conducting field tests, two HER units were used to obtain RRf values for DEM, using IS #2 and the three labelled DEM standards as normalization factors. Data from HER units 112 and 121 (112 and 121 being instrument designation numbers) were averaged and RRf values against IS #2 were determined (2.588±0.415). RRf values between unlabeled DEM and its isotopic analogues were verified to be at or very near 1 (0.9622±0.0556). All RRf values were determined using the formula:

$$RRF = A_x C_{is} / A_{is} C_x$$

where RRf is the relative response factor, $A_x$ is the area of the primary ion for the compound to be measured (counts), $A_{is}$ is the area of the primary ion for the internal standard (counts), $C_{is}$ is the amount of internal standard or focusing agent loaded (ng) and $C_x$ is the amount of the $DEM_{115}$ in the calibration standard (ng).

To calculate RRfs using the HER IS #2 compound, it was helpful to determine the static amount of IS #2 that was injected onto the GC/MS for each run as this is not provided by the instrument manufacturer. To calculate, stable isotope labelled BPFB (bromopentafluorobenzene) was pre-loaded onto TD tubes and the IS #2 concentration was determined relative to the response of known quantities of labelled BPFB. A total of seven samples were analyzed using three different HER units, which yielded a value of 50 ng per sample with a standard deviation of less than 3 ng. IS #2 was quantified using the extracted ion chromatogram for m/z 117 and DEM peak areas were determined using extracted ion chromatograms based upon the primary fragment in electron ionization mass spectrometry, which corresponded to m/z values of 115, 116, 117 and 118 for the four respective isotopic analogues of DEM.

The TD tube samples were prepared at Wright-Patterson Air Force Base ("WPAFB") for deployment to the seven remote field locations. The TD tubes were pre-loaded with three isotopic analogues ($DEM_{116}$, $DEM_{117}$, and $DEM_{118}$) having 1-3 $^{13}C$ atoms to allow for their distinction by the mass spectrometers. $DEM_{115}$ was separately loaded as a control. $DEM_{116}$, $DEM_{117}$, and $DEM_{118}$ were pre-diluted to desired concentrations using acetonitrile and loaded onto the TD tubes using a calibration solution-loading rig (Markes International; Sacramento, CA, USA) with a static flow of nitrogen at 50 mL/min. Each three-point, in situ curve was composed of $DEM_{116}$, $DEM_{117}$, and $DEM_{118}$ at 25 ng, 49.7 ng, and 75.5 ng, respectively. After loading, acetonitrile was purged by holding the TD tubes at 50° C. and flushing with $N_2$ for 90 min at 50 mL/min to 75 mL/min. $DEM_{115}$ was diluted into methanol and loaded at varying concentrations using the same methodology. Post analysis, linear regression was performed on each three-point calibration independently and the derived equation used to calculate the amount of $DEM_{115}$ measured from each TD tube.

Over six months, a set of three, pre-loaded TD tubes plus one blank was sent to each of seven field locations throughout the continental United States; one set of three, pre-loaded TD tubes plus one blank were retained at WPAFB as a control sample set. When each location received the TD tube samples, the TD tubes were stored at ambient temperature until analysis. Initial sample sets included a cover letter with written and graphic instructions for installation and use of the TDSS, a factory-preconfigured HER method (CWA method; TD_Tenax_Tribed_310C; Inficon), a spreadsheet configured to extract ion chromatograms of the target compounds, and two slide decks giving instructions on returning data input and spreadsheet generation. TD tube sample sets were sent out on a bi-monthly basis for a total of three times to complete the field study.

Samples were analyzed within 1 to 134 days after loading. Metadata collected at the time of analyses requested the date, barometric pressure, ambient temperature, and location altitude. GC/MS conditions were based upon the factory method for CWA analysis and used a 100% polydimethylsiloxane column (15 m×0.25 mm ID; 1.0 μm film thickness). The column temperature, membrane, and valve oven were set at 60° C., 120° C., and 120° C., respectively, and the temperature of the TDSS was set to 310° C. The TDSS was initiated at 40° C. and ramped to the maximum temperature at 1.5° C./s. Total TDSS desorption time was 10 min. The initial GC oven temperature was 60° C. for 1.25 min and was increased to 90° C. at a rate of 8° C./min followed by an increase to 200° C. at 25° C./min. This was held for 6.1 min, which resulted in a total GC run of 15.3 min. Nitrogen ($N_2$) carrier gas was run in a constant pressure mode (88 kPa). The mass spectrometer was operated in electron impact ionization mode with a collisional energy of 70 eV and a scanning range of 45 m/z to 300 m/z with a dwell time of 300 ms, which resulted in a scan rate of 0.765 scan/s. HER internal standards 1,3,5-tris-(trifluoromethyl)benzene (IS #1, 10.7 ppm) and bromopentafluorobenzene (IS #2, 5.5 ppm) were added automatically to the sample inlet flow at a 1:10 split ratio during each cycle.

The DEM curves were established on two HAPSITE instruments at a contractor facility one year prior to the testing described here so as to demonstrate transportability of the curves to field location testing sites. Calculations for percent recoveries for the testing described here are based on the previously established DEM curves.

All data acquisition and peak area determinations were done using the HAPSITE-ER IQ software package (v. 2.32, Inficon). Tentative compound identifications were found using the HAPSITE-ER IQ software. Data analysis was performed in Prism GraphPad (GraphPad Software Inc., La Jolla, CA, USA) and Microsoft Excel 2016 (Redmond, WA, USA). Datasets were analyzed for statistical outliers using the Prism GraphPad ROUT algorithm with a false discovery rate (Q value) of 1%.

To evaluate conventional calibration methods with methods according to embodiments of the present invention. The net result is a comparison of analyte recovery values using four calibration schemes and previously established curves: (1) RRf calibration using HAPSITE-ER IS #2-IS #2 RRf; (2) External calibration run on representative instruments—external calibration; (3) Isotopic standard curves pre-loaded on each TD tube—isotopic calibration; and (4) RRf calibration using $DEM_{116-118}$-$DEM_{116}$ RRf, $DEM_{117}$ RRf and $DEM_{118}$ RRf.

There were frequent disparities observed in the IS #2 distribution of peak areas as compared to the other analytes. Though IS #2 showed a minimal interquartile range, instances when the HAPSITE failed to deliver the intended amount of this calibrant led to a large number of outliers. Owing to the distortion of the y-axis resulting from IS #2 variability, moderate stringency outlier analysis (Q=1%) was conducted on all sets of raw peak areas using the ROUT algorithm, which identified six outliers for IS #2 and no outliers for the other analytes. When the outliers were removed, a better representation of the actual distributions appeared.

Figure 11:
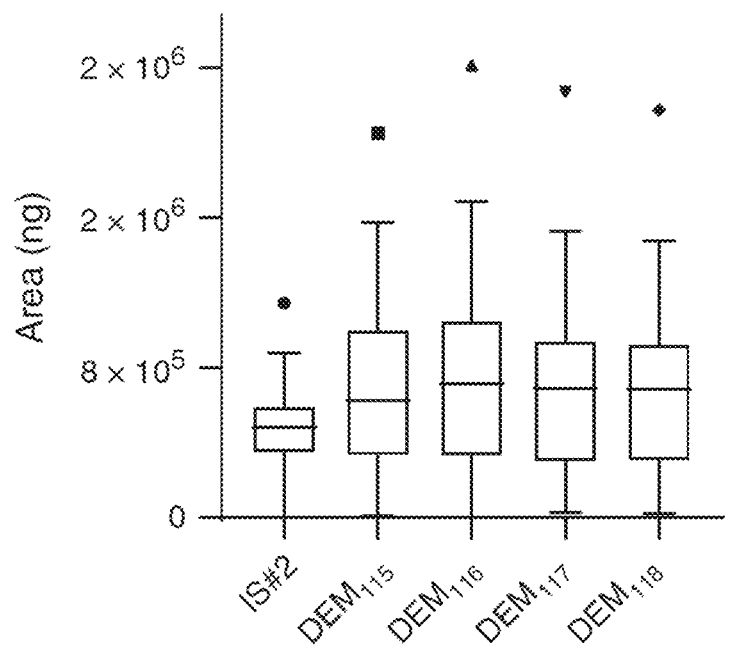
Figure 12:
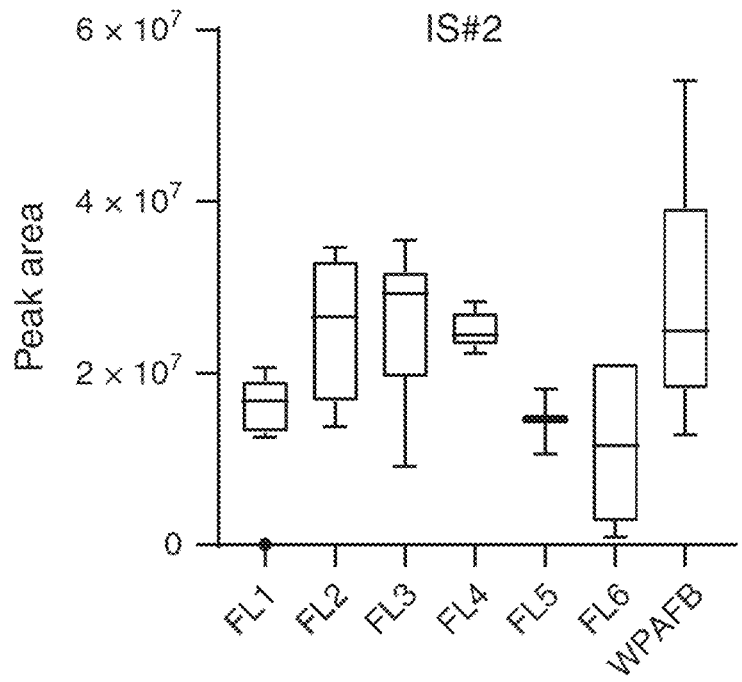
FIG. 12 graphically illustrates a distribution of peak area responses for IS #2 separated by field location and with outliers removed.
Figure 13A:
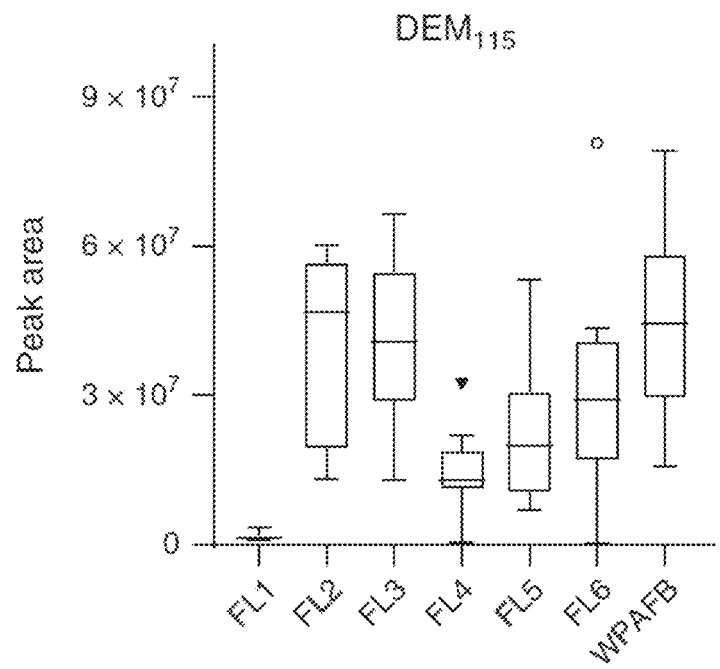
FIG. 13A graphically illustrates a distribution of peak area responses for $DEM_{115}$ separated by field location and with outliers removed.
Figure 13B:
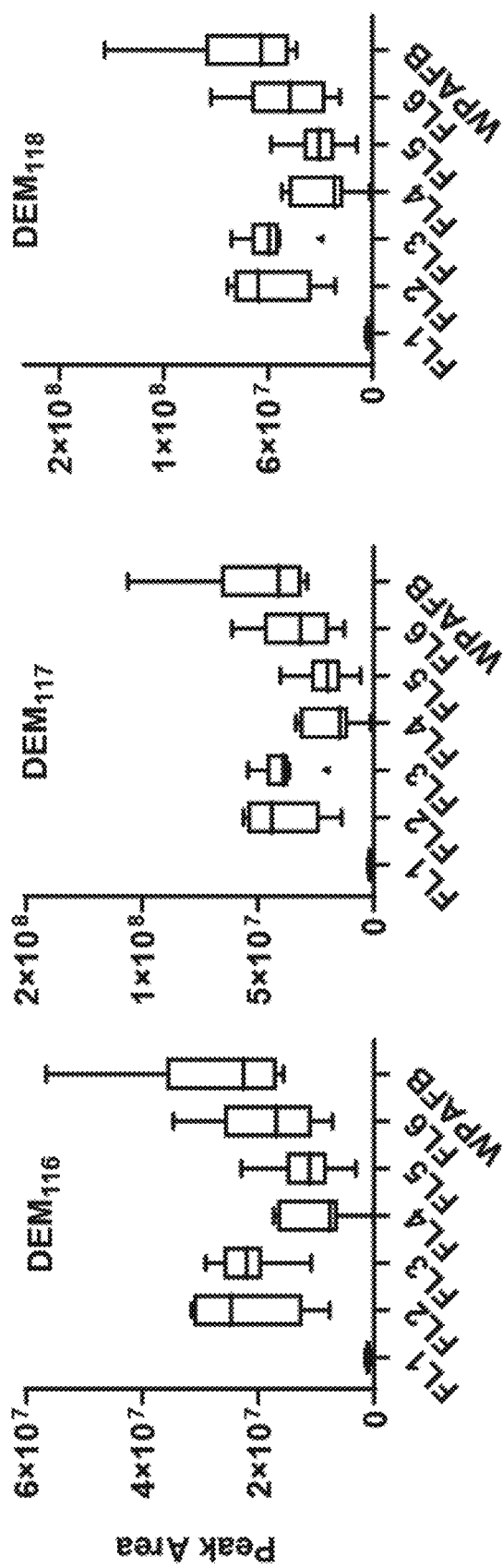
FIG. 13B graphically illustrates distributions of peak area responses for $DEM_{116}$, $DEM_{117}$, and $DEM_{118}$ separated by field location and with outliers removed.

FIG. 11 demonstrates a rise in ladder effect from the loading of 25 ng, 50 ng, and 75 ng for $DEM_{116}$, $DEM_{117}$, and $DEM_{118}$, respectively. For normalization purposes, and as shown in FIG. 12, response factors for all analytes were calculated by dividing the peak area by the amount (ng) loaded with each sample, which yielded an improved representation of the responses when the data from multiple instruments were plotted together. This transformation allowed comparison of the distribution of responses for each isotopic analogue, regardless of the amount loaded. FIG. 13 illustrates the distribution of IS #2 responses for each field location (outliers removed). When outliers were included, it was easy to identify instruments with problematic IS #2 dosing. This analysis allowed the observation that while the FL #5 data were produced by two instruments, one of the two was not functioning properly and apparently dispensed more than 10-fold the average amount of IS #2. This anomaly was not the result of detector variability as no other peak area values showed the same difference between the two instruments.

Figure 14:
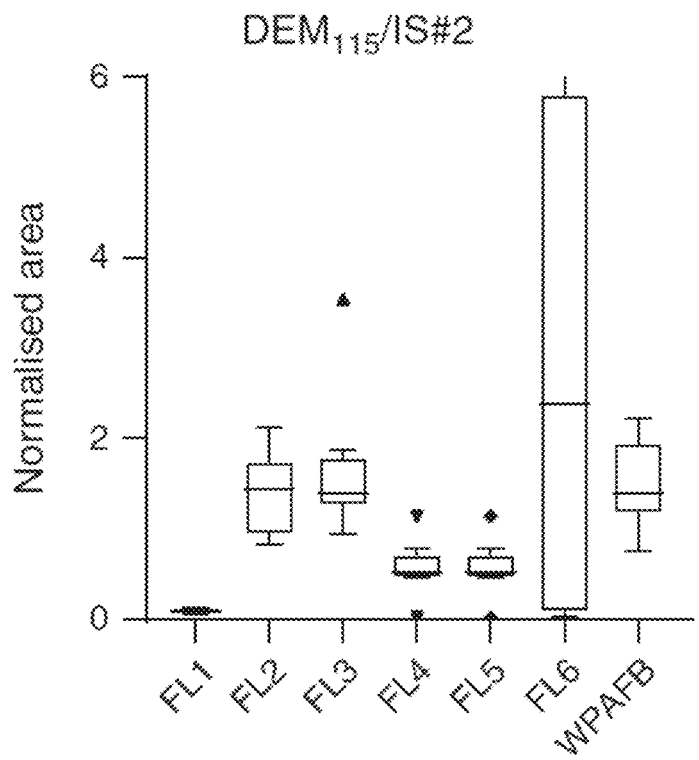
FIG. 14 graphically illustrates distributions of peak area responses for $DEM_{115}$ separated by field location and normalized by IS #2.

The use of focusing agents eliminated any negative impact of this anomaly on the calculated recovery values. Peak area distributions for each analyte grouped by field sampling location (FIGS. 14A and 14B) illustrated a variable detector response to identical samples; greater than 60% overlap between instrument response ranges were observed between each calibration level (the three isotopic analogues of DEM in FIG. 11), despite the fact that the analogues should present identical response factors. Note, however, that the response ranges on any given instrument were similar for all isotopic analogues of DEM. These data highlight the difficulty in obtaining accurate quantification using the typical factory calibrations included in the software sold with portable instrumentation.

Figure 15C:
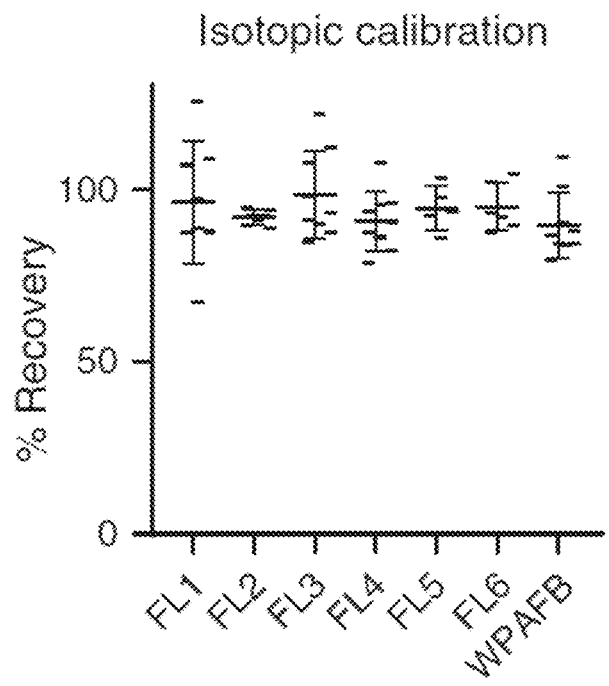
FIGS. 15A-15C are scatter plots illustrating analyte recovery variability for IS #2 RRF, external calibration, and isotopic calibration, respectively, separated by field location.
Figure 15A:
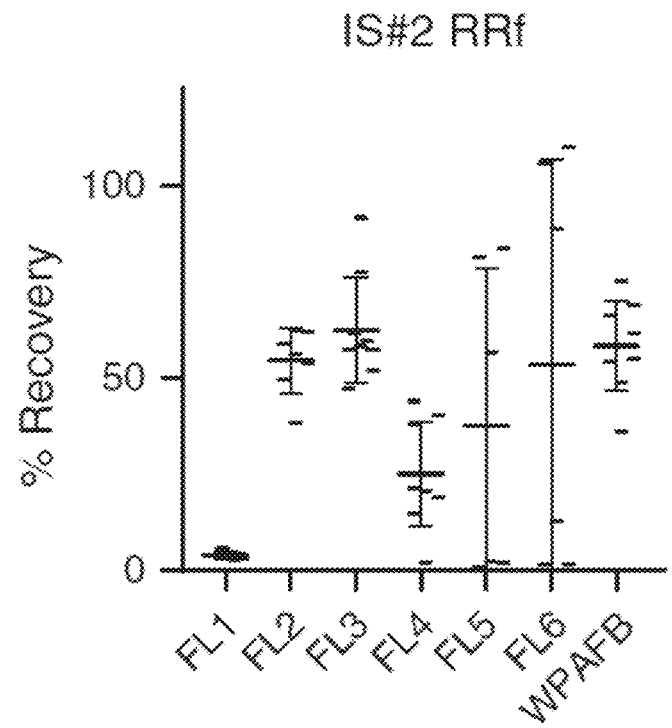
Figure 15B:
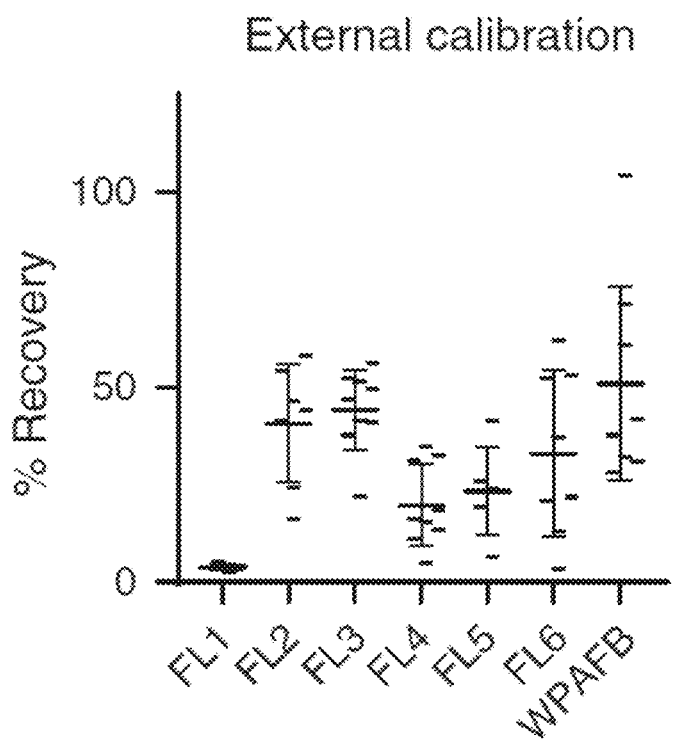

FIG. 15 illustrates the result of normalizing the responses of analytes by IS #2. In most cases IS #2 was capable of imparting a level of stability to the analyte data. Reliance on this method for normalization requires a level of fidelity not observed on the HER. The standard deviation between IS #2 RRfs for two instruments (16.0%) guaranteed a minimum distortion of the quantitative data that was nearly unacceptable without accounting for additional sources of error that are typical in field experiments. Furthermore, in instances when anomalies were observed in both IS #2 and $DEM_{115}$ responses, the FL #6 normalized data were heavily skewed despite all of the sample data from that location being generated from one instrument.

Figure 16:
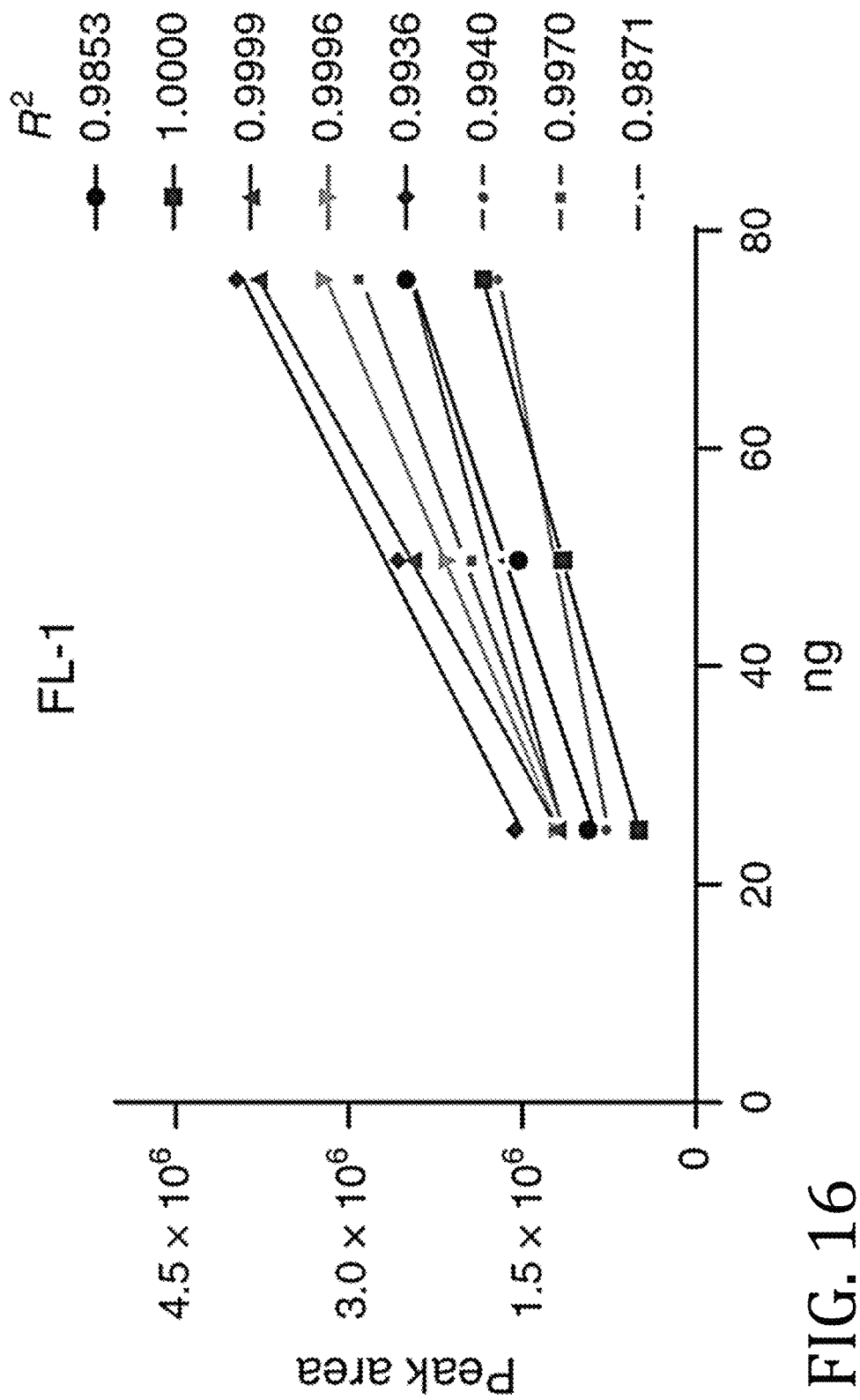
FIG. 16 is a graphical representation of the isotopic calibration linear regression analysis from a representative field location.

The variability of IS #2 for each field location suggested malfunctioning equipment being run at FL-5 and FL-6. FIG. 16A demonstrates how a disparity in the mean IS #2 peak areas between fielded instruments can lead to additional discrepancies between derived and actual recoveries when an RRf that has been calculated by reach-back laboratory facilities is employed.

The focusing agents on the TD tubes differed from the more typical internal standards in that they were added to the TD tubes before any handling in the field; therefore, the focusing agents were able to compensate for the entire range of conditions that typically degrade the recovery of sampled volatiles.

The mean recovery value (n=26) calculated using the IS #2 RRf was 90.0%; however, the standard deviation and range values were 248.7% and 1733%, respectively. Inspection of the sample recovery statistics for IS #2 demonstrated that a handful of outliers nearly doubled the mean recovery value.

Recoveries computed using the external standard calibration averaged 31.38% and a standard deviation and range of 21.4% and 101.9%, respectively. The danger implied by this type of result is that potentially hazardous substances may be underestimated in the field and lead to toxic exposures or ignorance of potentially hazardous concentrations of VOCs or overestimated and lead to unnecessary delays.

Mean recoveries calculated using isotopic calibration, $DEM_{116}$ RRf, $DEM_{117}$ RRf, and $DEM_{118}$ RRf were 93.4±18.3%, 94.5±64.9%, 93.9±16.9% and 95.2±17.2%, respectively. It is notable that the large range and standard deviation values for recoveries calculated using $DEM_{116}$ RRf were heavily skewed by a single outlier having a value of 556.3%. Nonetheless, these recovery values were more than acceptable in a deployed setting and provided definitive quantitative measurements from this portable instrument without more complex statistical analyses. However, a comparison of recoveries between each field location summarized the lack of consistency in IS #2 responses for the IS #2 RRf method (FIG. 16A) and quantification using an external calibration (FIG. 16B) in contrast to the more robust, relatively stable responses obtained using the isotopic calibration (FIG. 16C). This was further illustrated when the data were normalized by only one of the isotope-labelled standards (see, Supplemental Data for QUALLEY et al., "Data quality improvement for field-portable gas chromatography-mass spectrometry through the use of isotopic analogues for in-situ calibration," *Environ. Chem.* (2019), DOI: 10.1071/EN19134.

In the field, it is highly unlikely that the bioenvironmental engineer or technician user of the HER system 40 will perform an outlier analysis on the entire dataset produced. Therefore, the ability of focusing agents pre-incorporation onto TD tubes to provide highly robust data was evaluated. With outliers removed, the descriptive statistics showed much improved stability, which allowed for a more accurate comparison of the calibration methods. All descriptive statistics for percent recovery values with and without outlier values are shown in Tables 2 and 3. Outlier analysis resulted in removal of three values for IS #2 RRf, isotopic curve, and $DEM_{117}$ RRf datasets; six outliers removed from the $DEM_{116}$ RRf set; and two removed from $DEM_{118}$ RRf data. No outliers were identified in the percent recovery data obtained from external calibration. Interestingly, IS #2 RRf mean recoveries were artificially inflated by the outliers, although this analysis would typically not be available on-site for the end user of field portable instrumentation.

While removal of the outlier values greatly improved the consistency of the IS #2 RRf data, poor recoveries were revealed (mean=42.8±30.4%). External calibration data were unchanged as no outliers were identified. Mean recoveries calculated using isotopic calibration, $DEM_{116}$ RRf, $DEM_{117}$ RRf, and $DEM_{118}$ RRf calibrations averaged 93.8±10.5%, 86.5±7.4%, 94.2±9.4%, and 96.1±10.3%, which were relatively unchanged from the original values. This effectively highlighted the effectiveness of the focusing agents when used by field personnel for whom such statistical analyses would be unavailable.

Figure 17A:
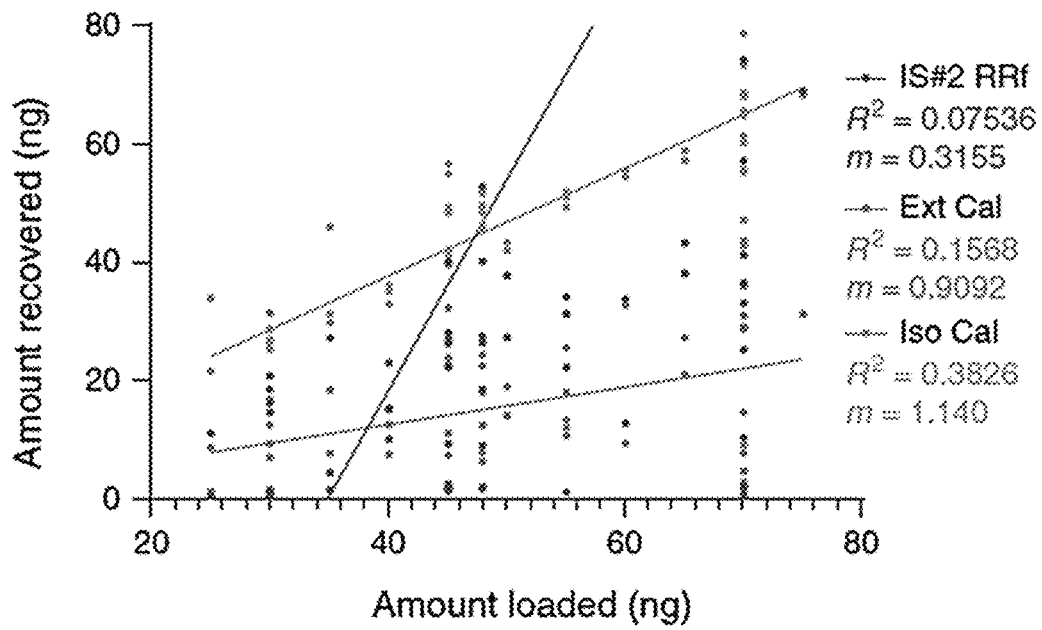
FIGS. 17A and 17B graphically illustrate linear regression analyses for IS #2 RRF, external calibration, and isotopic calibration with computed recoveries plotted against amount loaded on each TD tube (outlier removed in FIG. 17B).
Figure 17B:
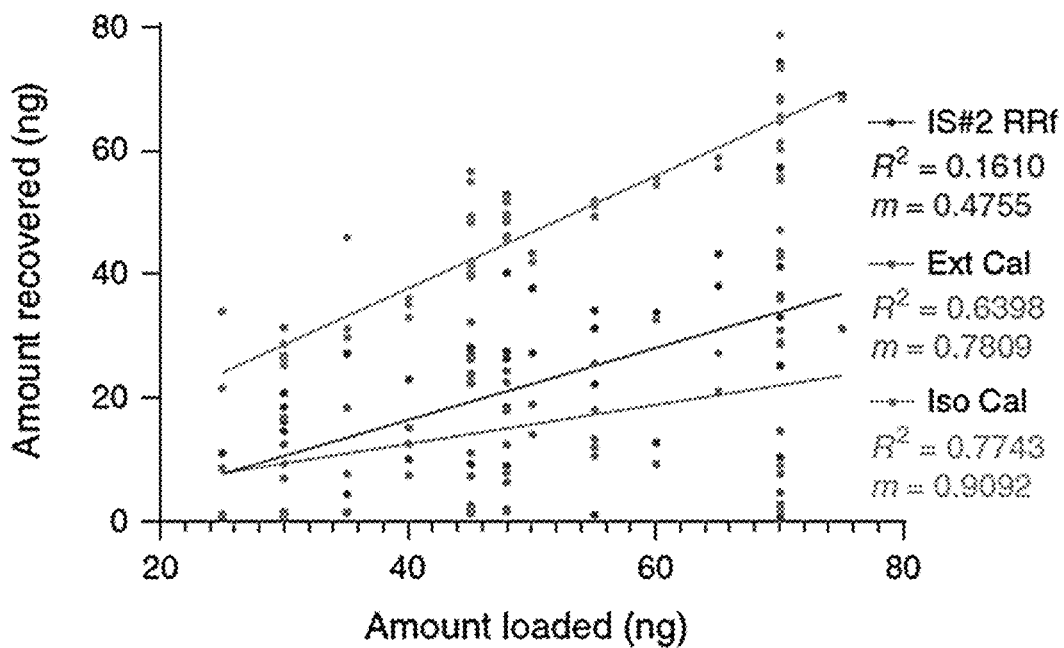

Since each TD tube included an isotopic DEM standard curve, it was possible to calibrate each HER system 40, individually, on a per sample basis. An example plot of linear regression is shown for one location alongside the calculated $R^2$ value (FIG. 17). While having only a few calibration points somewhat limits the use of regression analysis, the data support the practice of using as little as three calibration levels for in situ calibration. The lowest mean $R^2$ value (0.9981) with the highest standard deviation (0.0342) was observed from FL-4, where one TD tube yielded extremely low responses from all of the DEM isotopic analogues despite a typical IS #2 response—likely indicating a leak at the TDSS. While most calculated recoveries from this sample were entirely aberrant from the norm, recoveries calculated from isotopic calibration (135.6%), $DEM_{117}$ RRf calibration (79.7%) and $DEM_{118}$ RRf calibration (96.1%) still provided useful data from the sample. It is notable that the prescribed method using IS #2 estimated $DEM_{115}$ recovery at 1.9%. This is important because of how the HER functions with respect to IS #2 loading and tube desorption wherein a leak at the TDSS leads to reduced analyte responses versus a greatly increased IS #2.

Figure 18A:
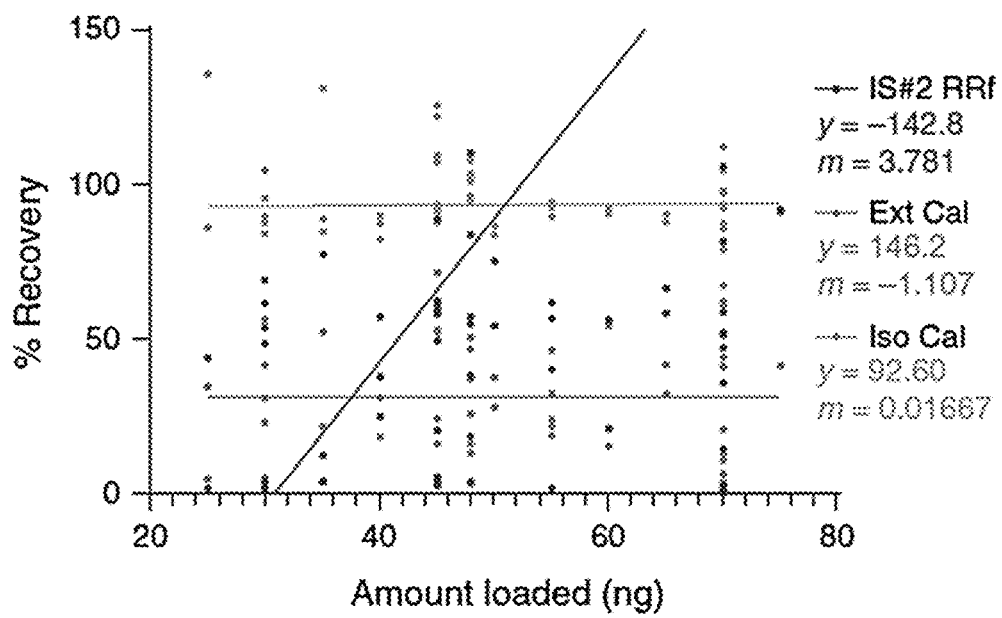
FIGS. 18A and 18B graphically illustrate linear regression analyses for IS #2 RRF, external calibration, and isotopic calibration with computed recoveries plotted against amount loaded on each TD tube (outlier removed in FIG. 18B).
Figure 19:
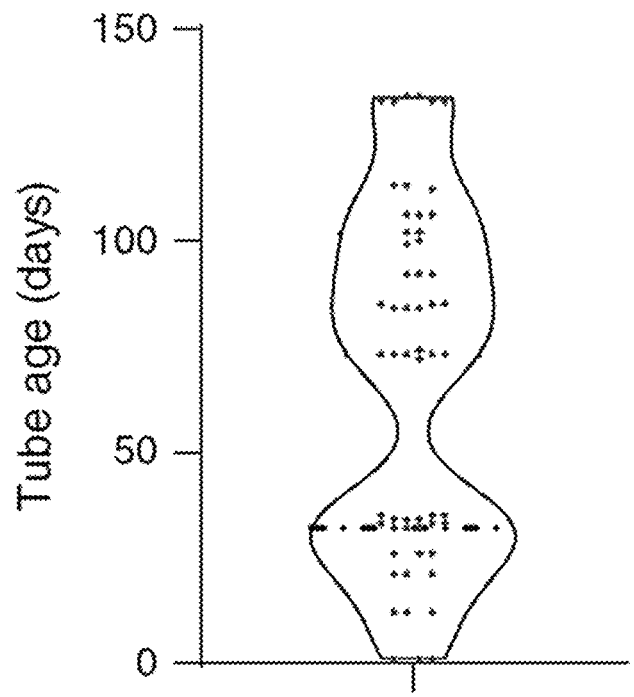
FIG. 19 is a violin plot illustrating a distribution of storage times for analyzed TD tubes with individual sample ages shown with dots.

Linear regression analyses provided a useful method for comparing the calibration methods. FIGS. 18A and 19A are scatter plots setting an amount loaded versus amount recovered and an amount loaded versus percent recovered, respectively, containing all 56 data points. In this figures, the skewing of IS #2 recoveries was dramatic, as was the impact on the slope of $DEM_{116}$ arising from the presence of the outliers (see FIG. 18A). In a typical field sampling setting, especially when used by first responders and in military applications, data outliers would be treated as prima facie evidence of the quantities and exposure levels for potentially hazardous substances. This is particularly problematic when IS #2 RRf calibration is employed since all six of those outliers, which showed abnormally elevated peak area values for IS #2, would result in a drastic underestimation of analyte concentrations.

TABLE 2

|  | IS#2 RRF | External Calibration | Isotopic Calibration | $DEM_{116}$ RRF | $DEM_{117}$ RRF | $DEM_{118}$ RRF |
| --- | --- | --- | --- | --- | --- | --- |
| Number of Values | 56 | 56 | 56 | 56 | 56 | 56 |
| Minimum | 0.45 | 2.60 | −3.79 | 1.37 | 1.40 | 1.42 |
| 25% Percentile | 13.07 | 13.82 | 87.53 | 82.21 | 88.83 | 90.44 |
| Median | 52.99 | 31.16 | 92.28 | 85.40 | 93.18 | 95.18 |
| 75% Percentile | 62.39 | 46.78 | 100.3 | 91.48 | 98.93 | 100.8 |
| Maximum | 1734 | 104.5 | 135.6 | 556.3 | 131.6 | 138.2 |
| Range | 1733 | 101.9 | 139.4 | 554.9 | 130.2 | 136.7 |
| Mean | 89.97 | 31.38 | 93.44 | 94.56 | 93.86 | 95.19 |
| Standard Deviation | 248.7 | 21.37 | 18.29 | 64.89 | 16.89 | 17.20 |
| Standard Error of Mean | 33.24 | 2.856 | 2.444 | 8.671 | 2.258 | 2.299 |

TABLE 3

|  | IS#2 RRF | External Calibration | Isotopic Calibration | $DEM_{116}$ RRF | $DEM_{117}$ RRF | $DEM_{118}$ RRF |
| --- | --- | --- | --- | --- | --- | --- |
| Number of Values | 53 | 53 | 53 | 50 | 53 | 53 |
| Minimum | 0.45 | 2.60 | 67.23 | 69.83 | 71.95 | 74.28 |
| 25% Percentile | 9.060 | 13.82 | 87.54 | 82.60 | 88.95 | 90.47 |
| Median | 49.68 | 31.16 | 92.17 | 85.20 | 92.81 | 95.18 |
| 75% Percentile | 61.68 | 46.78 | 97.78 | 89.25 | 98.64 | 99.58 |
| Maximum | 110.2 | 104.5 | 125.5 | 106.7 | 122.6 | 128.6 |
| Range | 109.7 | 101.9 | 58.3 | 36.82 | 50.64 | 54.32 |
| Mean | 42.80 | 31.38 | 93.77 | 86.52 | 94.26 | 96.13 |
| Standard Deviation | 30.41 | 21.37 | 10.51 | 7.339 | 9.391 | 10.27 |
| Standard Error of Mean | 4.177 | 2.856 | 1.443 | 1.038 | 1.290 | 1.398 |

External calibration did not demonstrate the same variability of IS #2 RRf, but did demonstrate a poor average recovery (31.4%). This could lead to potentially underestimating the concentration of target analytes.

Figure 18B:
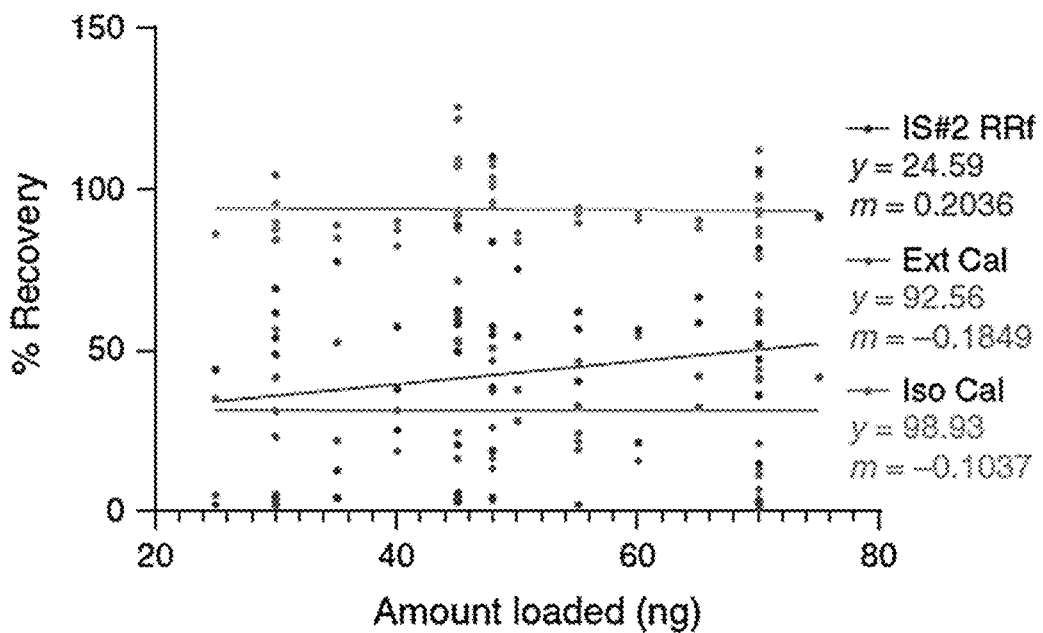

In FIGS. 18A and 18B, the regression analysis provided a broader view of the comparison—the perfect calibration would show an $R^2$ value of 1 (high level of agreement between replicate values) and the slope (m) would represent a 1:1 ratio between amount loaded and amount recovered. In FIGS. 19A and 19B, the slope and y-intercept values provided another comparison—the y-intercept approximates average recovery while the slope (m) indicates deviation from 100% recovery dependent on the loaded concentration. For an ideal analysis (recovery of 100%), the slope (m) value is 0 and the y-intercept value is 100.

Perhaps the most striking feature of the data graphically illustrated in FIGS. 18A-19B is the stability obtained using the focusing agent method when comparing the data with and without the outliers removed. While large shifts in the regressions were observed with the IS #2 methods, the focusing agents approach provided consistent results with values very near 100% for recovery.

Example 5

Figure 20:
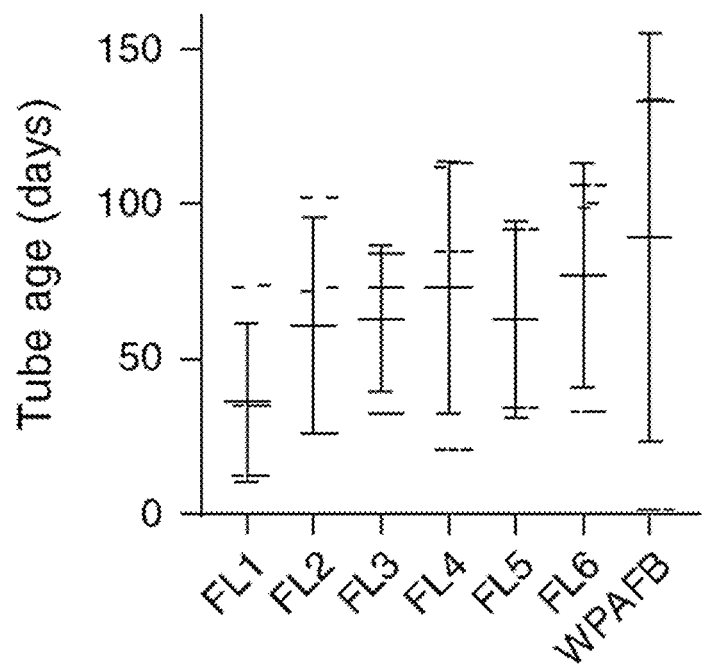
FIG. 20 is a scatter dot plot of individual TD tube storage times for each field location.

Field-deployed TD tubes were stored on average for 67 days before desorption and analysis. Distribution of storage periods across all tubes was illustrated with a violin plot in FIG. 20, and a sample tube age for each field location is illustrated in FIG. 21. During sample preparation, the TD tubes were loaded with isotopically labelled DEM at three concentrations and treated at 50° C. with a moderate flow of $N_2$ (50 mL/min to 75 mL/min) for 90 min to remove potential interferences arising from the acetonitrile diluent and to simulate the upper end of tube storage and handling conditions experienced in the field. Calculated recoveries of $DEM_{115}$ verified that there was no loss of DEM during treatment, which suggested stability of focusing agents on TD tubes under elevated temperatures of storage and transport (a loss of the isotopically labelled analytes would have manifested values exceeding 100% recovery in calculations using focusing agents as a normalizing factor). The relationship between tube age and calculated recovery for IS #2 RRf, External calibration, and isotopic calibration showed no significant correlation between computed values and tube storage duration.

Initially nine samples for each of eight field locations (72 total samples) were planned; however, the bulk of the data analysis presented here included only 56 total samples. Of the 16 samples omitted from analysis, nine samples represented one field location dropped entirely from the study owing to a total malfunction of the HER system 40. Only two samples yielded data from this field location while the remainder of the data was completely lost owing to an instrument failure that went undetected by the operators. All nine data points were stricken from this location because a representative sample set was not obtainable, and the location was not assigned a FL # in this study. A single data point from FL #1 was lost due to a depletion of carrier gas during the sample analysis. Two sample data points were omitted from FL #5 because instrument malfunctions resulted in missing values for $DEM_{115}$, which rendered data analysis impossible. Additionally, four samples yielding aberrant yet complete data were omitted from the analysis. Based upon experience with the HER system 40, it is believed that deviant values seen in those six samples were likely the result of a flow path leak that lead to incomplete loading of the analytes onto the concentrator or GC column. Regardless of the cause, the focusing agent method provided better accuracy in calculating the recoveries for these samples than IS #2 RRf or external calibration in all cases.

This study describes data quality improvement for the calibration of field equipment using in-situ calibration with isotopic analogues. The approach yields greatly improved performance and data approximating that produced by fixed-base laboratories. While RRf-based quantification is not ideal when the internal standard is metered onto sampling tubes by the HER (in its current iteration), pre-incorporation of standards onto TD tubes before field deployment allows accurate and reproducible quantification through RRf and compensates for problems that arise using workflows employed for mobile TD-GC/MS instrumentation in the field. We plan to extend this approach to a variety of key target compounds of concern. Use of focusing agents has demonstrated the ability to overcome common problems that arise using workflows employed in field portable use of TD-GC/MS instrumentation and extends the capabilities of such equipment while reducing the need for on-site analytical expertise. This approach is currently being used to establish relative response factors to chemical warfare agents to allow the field quantification of these highly toxic compounds without the need to handle the agents themselves.

While the present invention was illustrated by the description of one or more embodiments thereof, and while embodiments have been described in considerable detail, they are not intended to restrict or in any way limit the scope of the appended claims to such detail. For example, incorporating focusing agents into other sampling devices for other analytical techniques is envisioned. Additional advantages and modification will readily appear to those skilled in the art. The invention in its broader aspects is therefore not limited to the specific details, representative product and method, and illustrative examples shown and described. Accordingly, departures may be made from such details without departing from the scope of the general inventive concept embraced by the following claims.

What is claimed is:

1. A method of comparing amounts of a target analyte using calibration transportability, the method comprising:
   obtaining first and second thermal desorption tubes, the first and second thermal desorption tubes comprising:
   a sorbent; and
   a plurality of focusing agents loaded at known, relative amounts onto the sorbent, focusing agents of the plurality comprising a compound that chromatographically elutes within a retention time the same as a retention time of a target analyte and having a mass spectrum similar to a mass spectrum of the target analyte,
   wherein the first and second thermal desorption tubes are configured to be further loaded with a sample having the target analyte, the first and second thermal desorption tubes having the same focusing agents at the same known, relative amounts;
   desorbing said focusing agents in a chromatography and mass spectrometry instrument;
   after desorbing, injecting an internal standard into the chromatography and mass spectrometry instrument, wherein the internal standard is not a focusing agent of the plurality;
   acquiring a first sample having the target analyte with the first thermal desorption tube;

acquiring a second sample having the target analyte with the second thermal desorption tube;

on separate instruments, analyzing an amount of target analyte in each of the first and second samples; and comparing the amounts of the target analyte in each of the first and second samples.

2. The method of claim 1, wherein acquiring the first sample occurs at a first location and acquiring a second sample occurs at a second location at a distance away from the first location.

3. A method of comparing amounts of a target analyte using calibration transportability, the method comprising:

obtaining first and second thermal desorption tubes, the first and second thermal desorption tubes comprising:

a sorbent; and a plurality of focusing agents loaded at known, relative amounts onto the sorbent, focusing agents of the plurality comprising a compound that chromatographically elutes within a retention time the same as a retention time of a target analyte and having a mass spectrum similar to a mass spectrum of the target analyte, wherein the first and second thermal desorption tubes are configured to be further loaded with a sample having the target analyte, the first and second thermal desorption tubes having the same focusing agents at the same known, relative amounts;

desorbing said focusing agents in a chromatography and mass spectrometry instrument;

injecting an internal standard immediately prior to desorbing said focusing agents in a chromatography and mass spectrometry instrument, wherein the internal standard is not a focusing agent of the plurality;

acquiring a first sample having the target analyte with the first thermal desorption tube;

acquiring a second sample having the target analyte with the second thermal desorption tube;

on separate instruments, analyzing an amount of target analyte in each of the first and second samples; and comparing the amounts of the target analyte in each of the first and second samples.

4. The method of claim 3, wherein acquiring the first sample occurs at a first location and acquiring a second sample occurs at a second location at a distance away from the first location.

* * * * *